(12) United States Patent
Atoji et al.

(10) Patent No.: US 11,388,372 B2
(45) Date of Patent: Jul. 12, 2022

(54) BIOLOGICAL STATE DETECTING APPARATUS AND BIOLOGICAL STATE DETECTION METHOD

(71) Applicant: Nuvoton Technology Corporation Japan, Kyoto (JP)

(72) Inventors: Makoto Atoji, Fukui (JP); Tomohito Nagata, Kyoto (JP); Noritaka Shimizu, Hamburg (DE); Kazuaki Matsuda, Osaka (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 0 days.

(21) Appl. No.: 17/154,839

(22) Filed: Jan. 21, 2021

(65) Prior Publication Data

US 2021/0144339 A1 May 13, 2021

Related U.S. Application Data

(63) Continuation of application No. PCT/JP2019/023059, filed on Jun. 11, 2019.

(30) Foreign Application Priority Data

Jul. 23, 2018 (JP) .............................. JP2018-137998

(51) Int. Cl.
*H04N 7/18* (2006.01)
*A61B 5/024* (2006.01)
(Continued)

(52) U.S. Cl.
CPC ........... *H04N 7/18* (2013.01); *A61B 5/02427* (2013.01); *G01S 17/08* (2013.01); *G01S 17/89* (2013.01);
(Continued)

(58) Field of Classification Search
None
See application file for complete search history.

(56) References Cited

U.S. PATENT DOCUMENTS

2015/0238087 A1* 8/2015 Yamashita ........... A61B 5/7275
600/473
2016/0178734 A1 6/2016 Kawamura et al.
(Continued)

FOREIGN PATENT DOCUMENTS

JP 2017-140202 A 8/2017
JP 2018-89369 A 6/2018
(Continued)

OTHER PUBLICATIONS

International Search Report dated Aug. 27, 2619 in corresponding International Patent Application No. PCT/JP2019/023059, with English translation.
(Continued)

*Primary Examiner* — Eileen M Adams
(74) *Attorney, Agent, or Firm* — McDermott Will & Emery LLP

(57) ABSTRACT

A biological state detecting apparatus which generates biological information of a person, light sources which emit light having a first wavelength and light having a second wavelength, respectively, an imaging device which receives reflected light of the emitted light, a controller which controls the light sources, an arithmetic operator which reads out a first image and a second image from the imaging device and performs an arithmetic operation thereon, and a state estimator which generates the biological information of the person. The arithmetic operator generates a distance image based on the first image and the second image.

16 Claims, 12 Drawing Sheets

(51) Int. Cl.
    *G01S 17/08*         (2006.01)
    *G01S 17/89*         (2020.01)
    *H04N 5/225*        (2006.01)
    *H04N 5/232*        (2006.01)
    *G06V 20/59*        (2022.01)
    *G06V 40/10*        (2022.01)

(52) U.S. Cl.
    CPC ............ *G06V 20/597* (2022.01); *G06V 40/10* (2022.01); *H04N 5/2256* (2013.01); *H04N 5/23229* (2013.01)

(56) References Cited

U.S. PATENT DOCUMENTS

| | | | |
|---|---|---|---|
| 2016/0205306 A1* | 7/2016 | Wang | H04N 5/2353 348/135 |
| 2018/0054608 A1* | 2/2018 | Chen | H04N 5/23238 |
| 2018/0153422 A1 | 6/2018 | Watanabe | |
| 2019/0339369 A1* | 11/2019 | Fenton | G01S 17/894 |
| 2021/0110549 A1* | 4/2021 | Rubinstein | A61B 5/02416 |

FOREIGN PATENT DOCUMENTS

| | | | |
|---|---|---|---|
| WO | 2014/073645 A1 | 5/2014 | |
| WO | 2014/207983 A1 | 12/2014 | |

OTHER PUBLICATIONS

Wei Zeng, et al., "Infrared Video based Non-invasive Heart Rate Measurement," Proceedings of the 2015 IEEE Conference on Robotics and Biomimetics, Dec. 2018, pp. 1041-1046.

\* cited by examiner

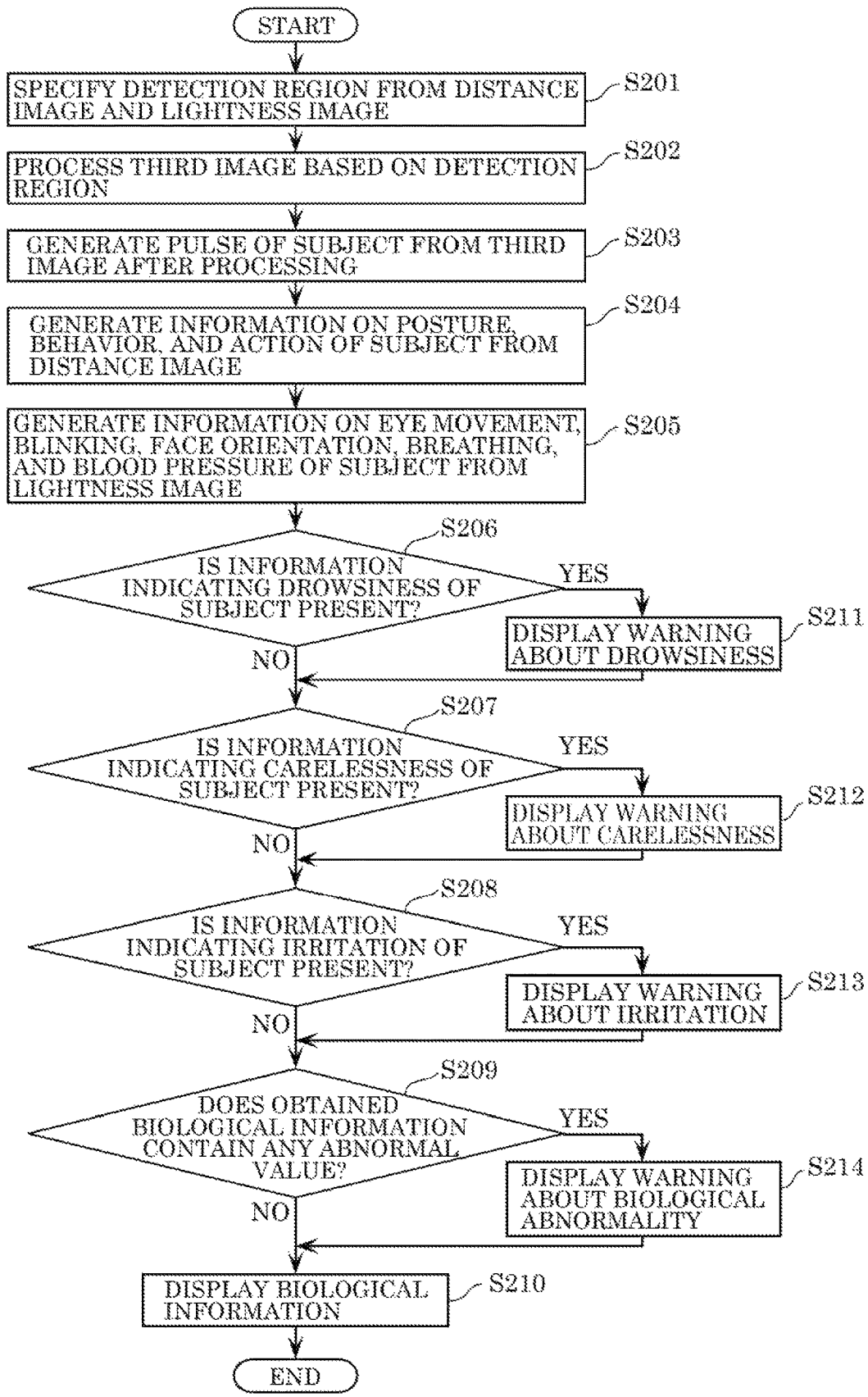

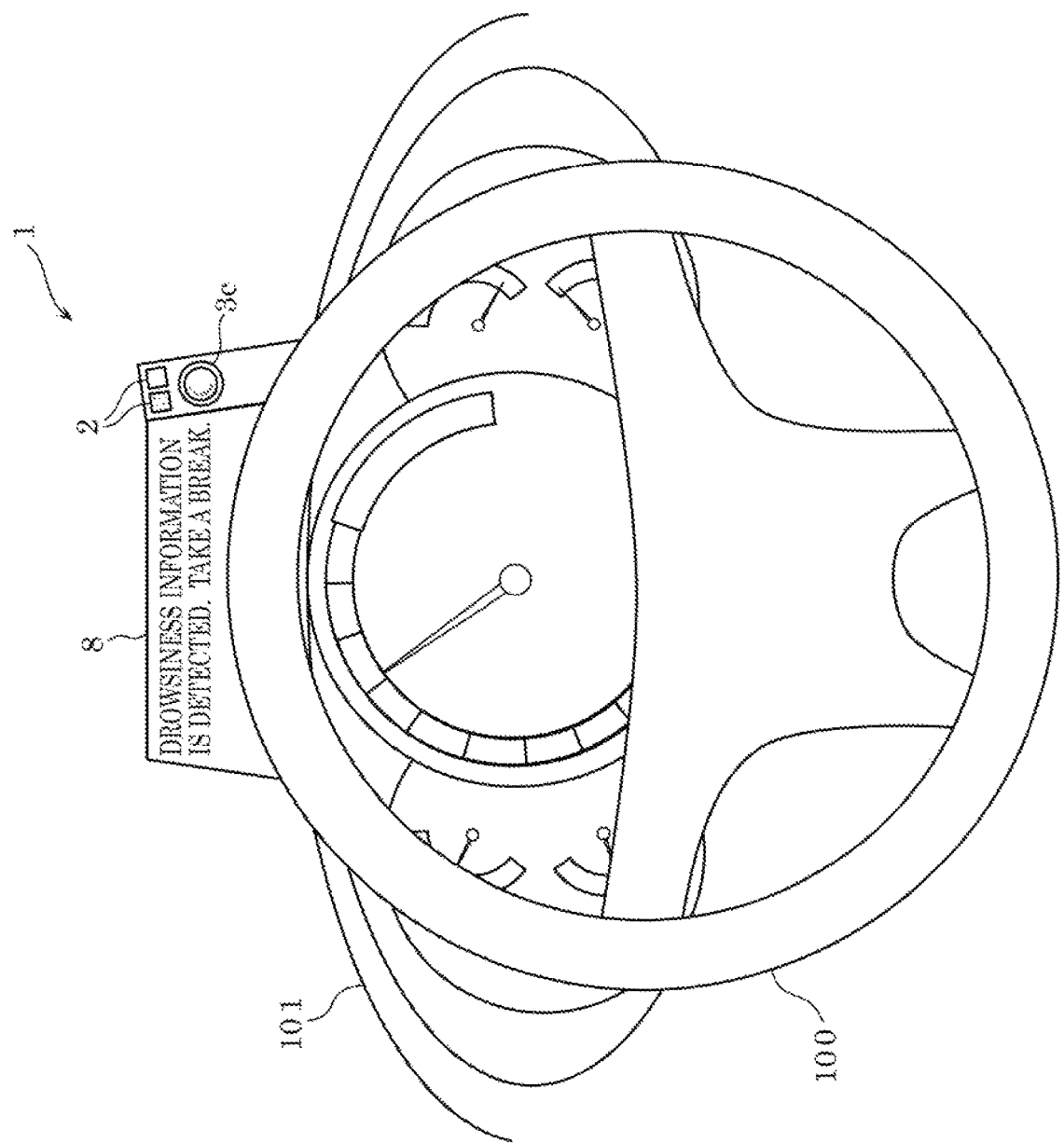

BIOLOGICAL STATE DETECTING APPARATUS AND BIOLOGICAL STATE DETECTION METHOD

CROSS REFERENCE TO RELATED APPLICATIONS

This application is a U.S. continuation application of PCT International Patent Application Number PCT/JP2019/023059 filed on Jun. 11, 2019, claiming the benefit of priority of Japanese Patent Application Number 2018-137998 filed on Jul. 23, 2018, the entire contents of which are hereby incorporated by reference.

BACKGROUND

1. Technical Field

The present disclosure relates to a biological state detecting apparatus and a biological state detection method, and particularly relates to a biological state detecting apparatus and a biological state detection method which detect the biological state of a subject by a non-contact method.

2. Description of the Related Art

There are demands for techniques of obtaining the biological state of a subject in a working environment to determine whether the subject is in a state suitable for the work. At this time, the biological state of the worker is desirably detected by a detector of a non-contact type not to disturb the work (for example, see Japanese Unexamined Patent Application Publication No. 2017-140202).

The technique disclosed in Japanese Unexamined Patent Application Publication No. 2017-140202 is one of techniques for non-contact detection of the biological state, and the disclosed pulse wave detector can reduce influences caused by movements of the body, enabling optical detection of the pulse wave with high detection precision.

SUMMARY

However, the pulse wave detector disclosed in Japanese Unexamined Patent Application Publication No. 2017-140202 simply detects the pulse wave based on images, and provides only a scant amount of information for comprehensive determination of the biological state.

The present disclosure has been made in order to solve the above problem. An object of the present disclosure is to provide a biological state detecting apparatus and a biological state detection method which can generate a larger amount of biological information using images than that generated by the related art.

To achieve the above object, one embodiment of the biological state detecting apparatus according to the present disclosure is a biological state detecting apparatus which detects a biological state of a person, the biological state detecting apparatus including: a first light source which emits light having a first wavelength; a second light source which emits light having a second wavelength different from the first wavelength; an imaging device including a plurality of elements which receive reflected light of the light emitted from the first light source and reflected light of the light emitted from the second light source, the light emitted from the first light source and the light emitted from the second light source being reflected by the person; a controller which controls the first light source and the second light source such that the first light source and the second light source alternately emit light; an arithmetic operator which generates a third image by reading out a first image and a second image from the imaging device, and performing an arithmetic operation on the first image and the second image, the first image being obtained through reception of the reflected light of the light emitted from the first light source, the second image being obtained through reception of the reflected light of the light emitted from the second light source; and a state estimator which generates biological information indicating a biological state of the person based on the third image generated by the arithmetic operator, and outputs the biological information. The arithmetic operator further generates a distance image based on at least one of the first image or the second image.

To achieve the above object, one embodiment of the biological state detection method according to the present disclosure is a biological state detection method of detecting a biological state of a person, the biological state detection method including: controlling a first light source which emits light having a first wavelength and a second light source which emits light having a second wavelength different from the first wavelength, such that the first light source and the second light source alternately emit light; generating a third image by reading out a first image and a second image from an imaging device including a plurality of elements which receive reflected light of the light emitted from the first light source and reflected light of the light emitted from the second light source, the light emitted from the first light source and the light emitted from the second light source being reflected by the person, and performing an arithmetic operation on the first image and the second image, the first image being obtained through reception of the reflected light of the light emitted from the first light source, the second image being obtained through reception of the reflected light of the light emitted from the second light source; and generating biological information indicating a biological state of the person based on the third image. In in the generating of the third image, a distance image is further generated based on at least one of the first image or the second image.

The present disclosure can be implemented not only as the biological state detecting apparatus and the biological state detection method, but also as a program causing a computer to execute steps included in the biological state detection method, as a recording medium, such as a computer-readable CD-ROM, having the program recorded thereon, or as information, data, or signals representing the program. The program, the information, the data, and the signals may be distributed through a communication network such as the Internet.

The biological state detecting apparatus and the biological state detection method according to the present disclosure can generate a larger amount of biological information using images than that in the related art.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

FIG. 11 is a flowchart illustrating the overall operation of the state estimator included in the biological state detecting apparatus according to the embodiment; and FIG. 12 is a diagram illustrating one example of the display of the warning by the biological state detecting apparatus according to the embodiment installed in an automobile.

DETAILED DESCRIPTION OF THE EMBODIMENTS

One embodiment according to the present disclosure will be described in detail with reference to the drawings. Embodiments described below all are preferred specific examples of the present disclosure. Numeric values, shapes, materials, components, arrangements and positions of the components, connection forms thereof, order of operations, and the like shown in the embodiments below are exemplary, and should not be construed as limitations to the present disclosure. Moreover, among the components of the embodiments below, the components not described in the present disclosure independent claim representing the most superordinate concept of the present disclosure will be described as arbitrary components that form more preferred embodiments.

First, the components according to the embodiment will be described with reference to FIG. 1.

Figure 1:
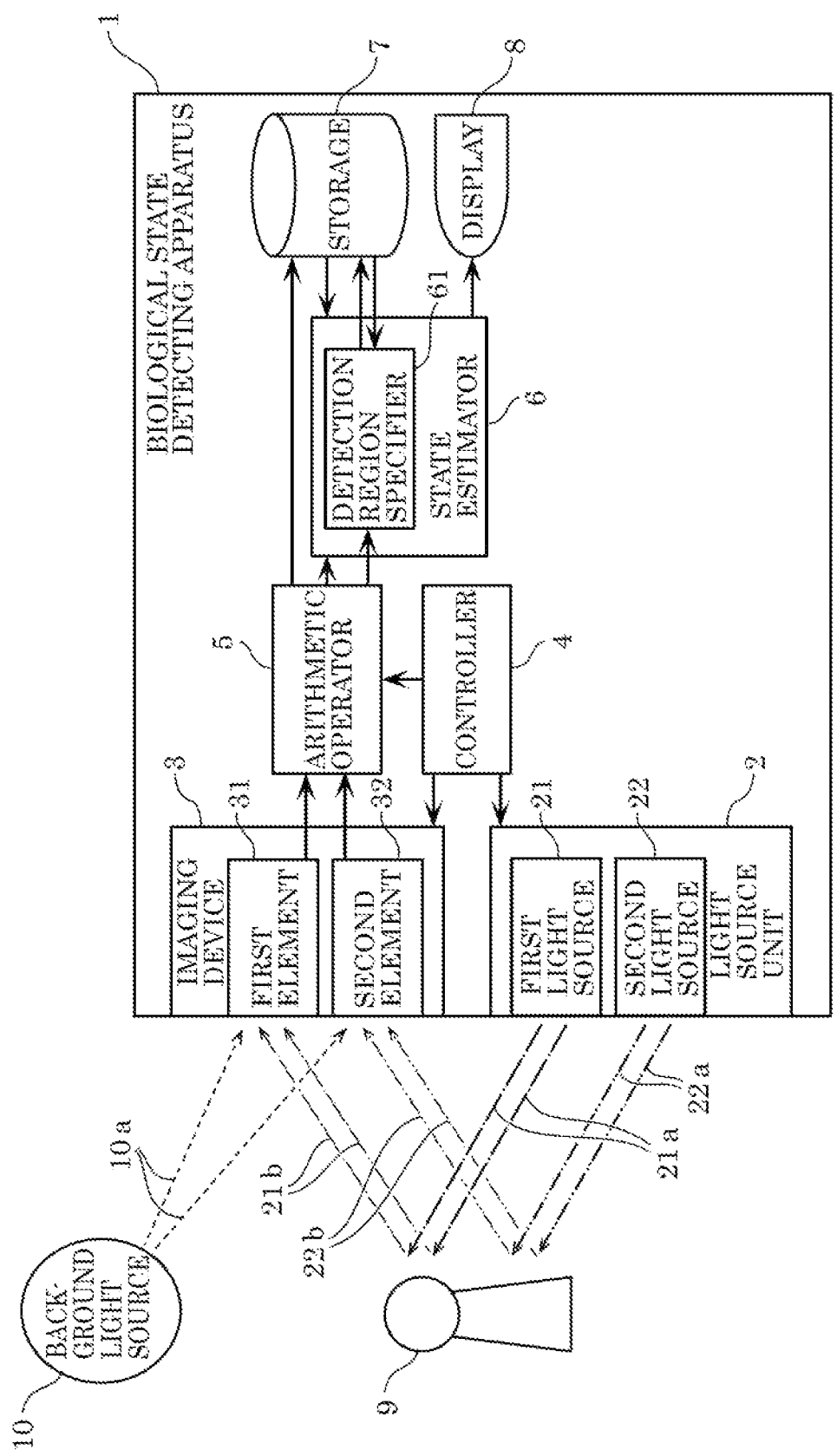
FIG. 1 is a functional block diagram of a biological state detecting apparatus according to an embodiment.

FIG. 1 is a functional block diagram illustrating biological state detecting apparatus 1 according to the embodiment. In addition to biological state detecting apparatus 1, FIG. 1 also illustrates person 9, which is a subject for detection of biological information. For emission light from light source unit 2 and reflected light of the emission light reflected by person 9, emission light 21a from first light source 21 and its reflected light 21b are indicated by arrowed dashed-and-dotted lines toward the traveling direction while emission light 22a from second light source 22 and its reflected light 22b are indicated by arrowed long dashed double-short dashed lines toward the traveling direction. Background light 10a radiated from background light source 10 onto imaging device 3 of biological state detecting apparatus 1 is indicated by the dashed line toward the traveling direction.

Biological state detecting apparatus 1 is an apparatus which detects the biological state of person 9, and is used as a physical condition monitor for person 9 as a detection target in a variety of environments, such as a driver who is driving an automobile, an operator for factory work, an office worker, or a student who is studying. Biological state detecting apparatus 1 includes light source unit 2, imaging device 3, controller 4, arithmetic operator 5, state estimator 6, storage 7, and display 8.

Light source unit 2 includes first light source 21 which emits emission light 21a having a first wavelength, and second light source 22 which emits emission light 22a having a second wavelength different from the first wavelength. First light source 21 and second light source 22 are each implemented with an independent light source (such as a semiconductor laser), and emit predetermined monochromatic light.

Imaging device 3 includes a plurality of elements which receive reflected light of the light emitted from first light source 21 and reflected light of the light emitted from second light source 22, the light emitted from first light source 21 and the light emitted from second light source 22 being reflected by person 9. Specifically, imaging device 3 is an image sensor, such as a complementary metal oxide semiconductor (CMOS) or a charge coupled device (CCD), which includes photoelectric converting elements implemented by photodiodes or the like. Imaging device 3 converts the received light into electric signals according to the light quantity. In the present embodiment, imaging device 3 is configured of first elements 31 for reflected light 21b (i.e., used to receive reflected light 21b) and second elements 32 for reflected light 22b (i.e., used to receive reflected light 22b).

Emission light 21a having a first wavelength, which is emitted from first light source 21, is reflected by person 9 and other objects within the imaging space, and as reflected light 21b having a first wavelength, enters at least first elements 31. Emission light 22a having a second wavelength, which is emitted from second light source 22, is also reflected by person 9 and other objects within the imaging space, and as reflected light 22b having a second wavelength, enters at least second elements 32. First elements 31 and second elements 32 are exposed to light in conjunction with the emission of the corresponding light sources and receive reflected light 21b and reflected light 22b, respectively, as well as background light 10a radiated from background light source 10, which is external light such as sunlight. First elements 31 and second elements 32 then generate charges through photoelectric conversion, and output the charges as electric signals.

Controller 4 is a processor which controls first light source 21 and second light source 22 such that first light source 21 and second light source 22 alternately emit light. Furthermore, controller 4 also controls imaging device 3 such that first elements 31 and second elements 32 are exposed to light in conjunction with the emissions of the corresponding light sources. More specifically, controller 4 is implemented with a ROM and a RAM on which control programs are stored, and a CPU which executes the control programs. Biological state detecting apparatus 1 also includes an inputter which receives an instruction from a user. Controller 4 may receive the instruction from the user through the inputter.

Arithmetic operator 5 is a processor which generates a third image by reading out a first image (obtained through reception of reflected light 21b of the light emitted from first light source 21) and a second image (obtained through reception of reflected light 22b of the light emitted from second light source 22) from imaging device 3, and performs an arithmetic operation on the read first image and second image. Specifically, arithmetic operator 5 is implemented with a ROM and a RAM in which arithmetic programs are stored, and a CPU which executes the arithmetic programs. The hardware such as these ROM, RAM, and CPU may be shared with the hardware which implements controller 4.

Arithmetic operator 5 is also a processor which generates a lightness image and a distance image based on one or both of the first image and the second image. The lightness image is an image configured of a group of pixel values representing lightness (that is, luminance). The distance image is an image configured of a group of pixel values representing the distance.

State estimator 6 is a processor which generates the biological information indicating the biological state of person 9 based on the third image generated by arithmetic operator 5. More specifically, state estimator 6 is implemented with a ROM and a RAM on which estimation programs are stored, and a CPU which executes the estimation programs. The hardware such as these ROM, RAM, and CPU may be shared with the hardware which implements controller 4.

State estimator 6 further includes detection region specifier 61 which specifies a detection region in the third image, which is a region used to generate the biological information. State estimator 6 generates the biological information using the detection region specified by detection region specifier 61.

Storage 7 is a memory which stores a face detection library for face detection needed to generate the biological information, and a variety of setting values including a distance reference value and a distance calibration value used to generate the distance image, and a threshold for comparison of the biological information. Storage 7 is implemented by a non-volatile memory or a magnetic disk. Furthermore, storage 7 also includes a volatile memory region for temporarily storing the generated image information during processing in state estimator 6.

Display 8 is a device which presents the state of person 9 estimated in state estimator 6 to one or both of person 9 and a manager who manages person 9, and is configured of a liquid crystal display, for example. For a simple notification to notify only a good or bad state of person 9, display 8 may be replaced with a simple device such as a warning light. Furthermore, in addition to or instead of display 8, a sound device (not illustrated) which buzzes or guides with a voice or a vibration device which sends a notification with vibration may be separately included to notify person 9 of the result of estimation output by state estimator 6.

All the components described above may be installed in a single housing; or light source unit 2 and imaging device 3 may be installed in a single housing while the remaining components may be implemented on a computer wiredly or wirelessly connected to the housing. Furthermore, display 8 may be separately connected to state estimator 6 in a wired or wireless manner, so that display 8 can be installed in a position more readily seen from the target person of the notification.

Although not illustrated, biological state detecting apparatus 1 includes a lens which converges reflected light 21b of the light emitted from first light source 21 and reflected light 22b of light emitted from second light source 22 onto imaging device 3, the light emitted from first light source 21 and the light emitted from second light source 22 being reflected by person 9.

The characteristics of the lens will now be described with reference to FIG. 2.

Figure 2:
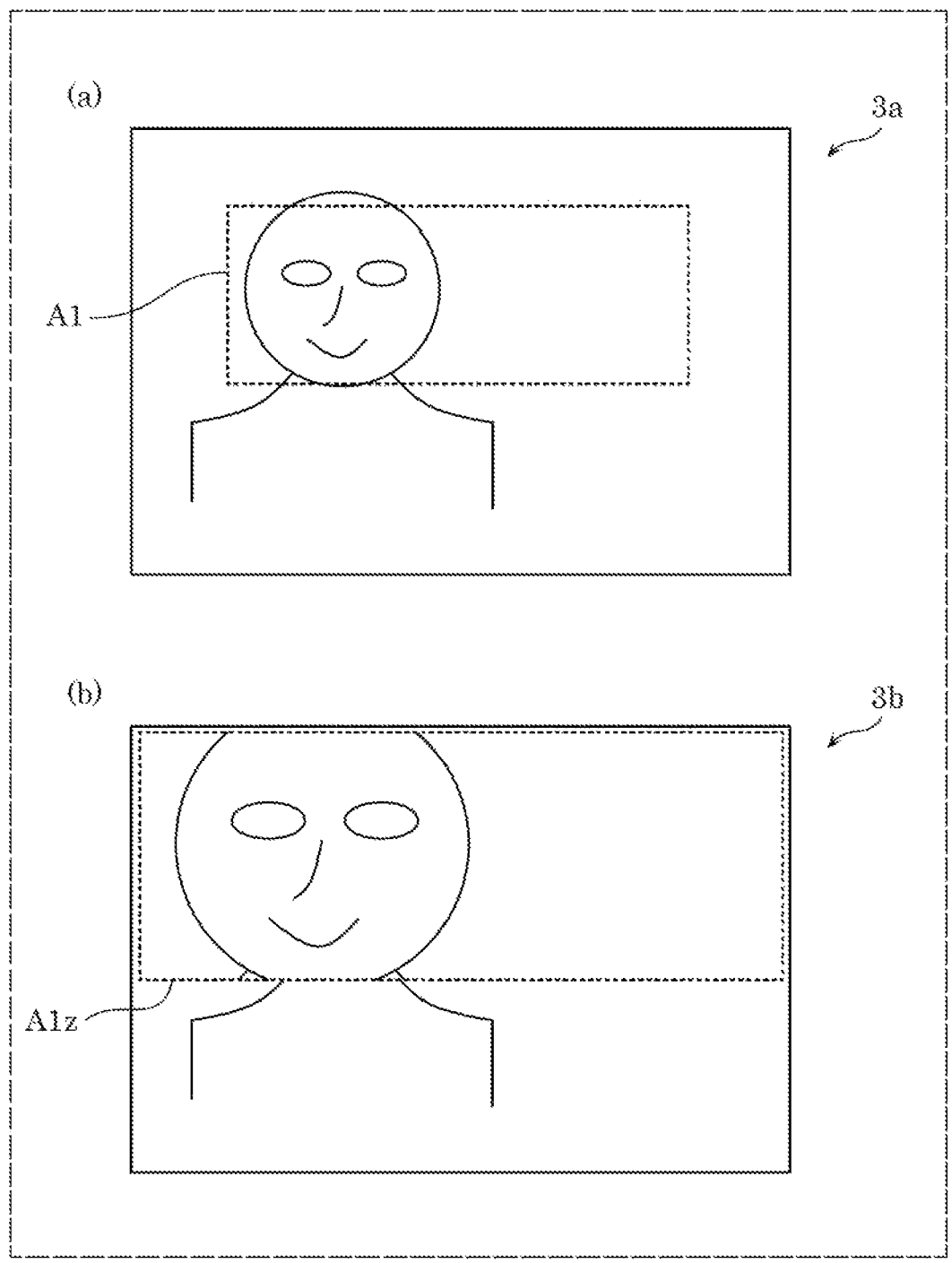
FIG. 2 is a diagram illustrating a projected image formed on an imaging device through a lens included in the biological state detecting apparatus according to the embodiment.

FIG. 2 is a diagram illustrating a projected image formed on imaging device 3 through the lens included in biological state detecting apparatus 1 according to the embodiment.

(a) of FIG. 2 illustrates projected image 3a formed on imaging device 3 when a standard lens has a spherical or non-spherical surface. (b) of FIG. 2 illustrates projected image 3b formed on imaging device 3 when a partially enlarging lens optically adjusted (i.e., a free-form surface lens) is used. As an example, person 9 present within the imaging space is reflected on projected images 3a and 3b.

In projected image 3a, the inside of the imaging space as seen is reproduced on the surfaces of the elements of imaging device 3, where the image of facial portion area A1 surrounded by the rectangular frame indicated by the dashed line and the image of the area outside facial portion area A1 are formed at the same magnification. In contrast, in projected image 3b, the image formed on imaging device 3 corresponds to the upper body of person 9. In this case, the lens is optically adjusted such that the portion corresponding to facial portion area A1z is enlarged. For this reason, projected image 3b has different magnifications (that is, different resolutions) between facial portion area A1z and the outside of facial portion area A1z.

Biological state detecting apparatus 1 according to the present embodiment may include the lens described in projected image 3a, or may include the lens described in projected image 3b in applications where the importance of the facial portion is assumed.

Next, the arrangement of light source unit 2 and imaging device 3 will be described in more detail with reference to FIGS. 3 to 5.

Figure 3:
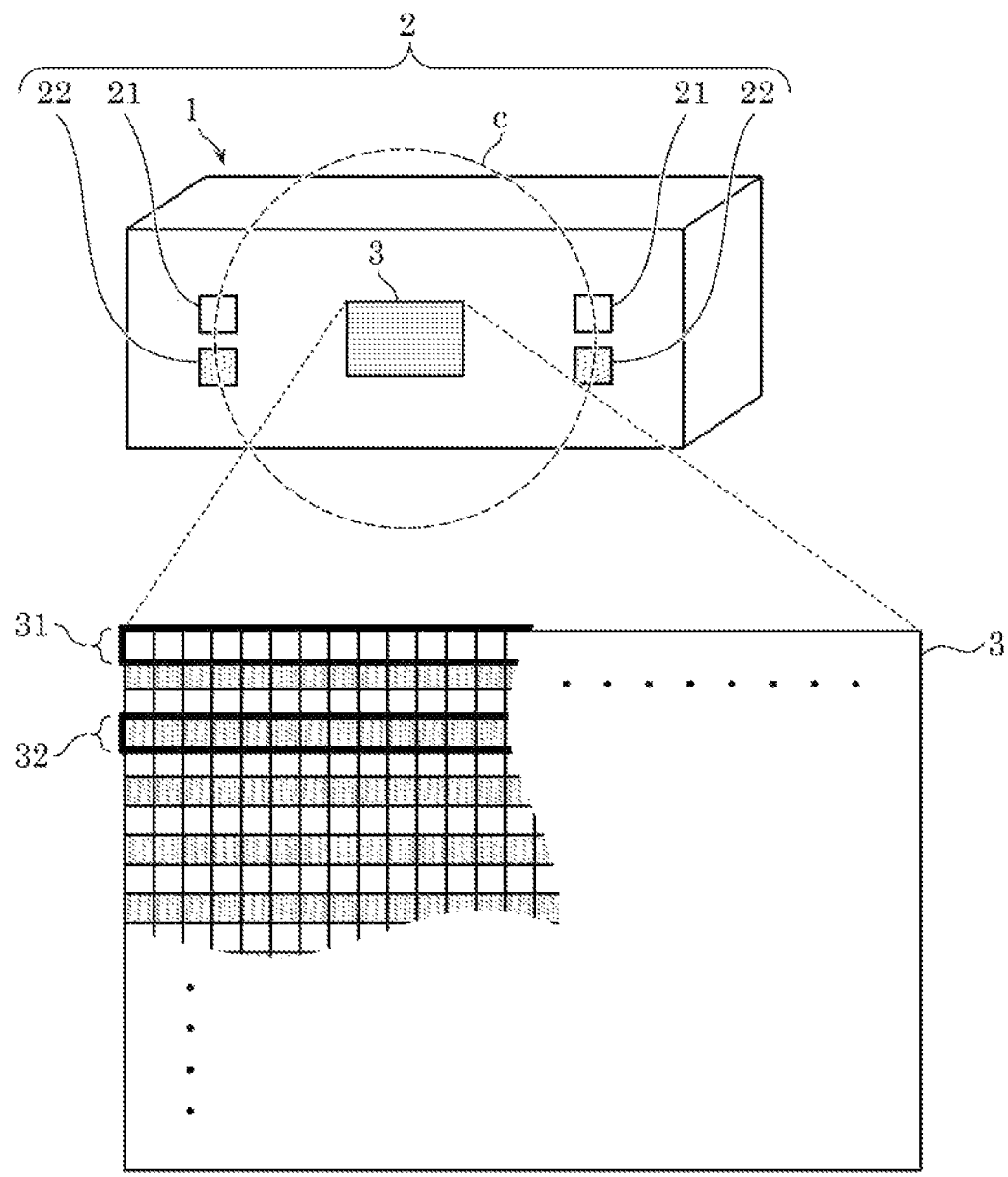
FIG. 3 is a diagram illustrating the positional relation between the light source unit and the imaging device arranged in the biological state detecting apparatus according to the embodiment.

FIG. 3 is a diagram illustrating the positional relation between light source unit 2 and imaging device 3 arranged in biological state detecting apparatus 1 according to the present embodiment.

In FIG. 3, the upper illustration shows a surface of biological state detecting apparatus 1 including light source unit 2 and imaging device 3 in planar view. In FIG. 3, the lower illustration shows an enlarged view of imaging device 3, where unit elements constituting imaging device 3 are aligned in a lattice form. In FIG. 3, the corners in the upper illustration are connected to the corresponding corners in the lower illustration with the dashed lines, respectively. In the lower illustration, the lattice surface formed of the unit elements is drawn only halfway for convenience.

In the upper illustration, first light source 21 and second light source 22 which constitute light source unit 2 are arranged at both ends of biological state detecting apparatus 1 to sandwich imaging device 3. First light source 21 and second light source 22 which constitute light source unit 2 are arranged coplanar with imaging device 3. At this time, first light source 21 and second light source 22 are arranged on circle c drawn around imaging device 3 to minimize the difference between first light source 21 and second light source 22 in the length of light path of emission light passing from the light source to an object and that of reflected light passing from the object to imaging device 3. To minimize the difference in the emission angle to the object which reflects the light, first light source 21 and second light source 22 are desirably arranged adjacent to each other as long as packaging allows. Light sources can be added to increase the light quantity of the emission light as long as pairs of first light source 21 and second light source 22 are arranged on circle c drawn around imaging device 3.

In imaging device 3, first element 31 and second element 32 are desirably arranged adjacent to each other in at least one of the vertical direction or the horizontal direction in planar view of imaging device 3 so as not to create an unbalanced arrangement of first elements 31 and second elements 32 corresponding to the light sources. In the present embodiment, as an example shown, imaging device 3 has an arrangement in a pattern of horizontal stripes such that a row of first element 31 and a row of second element 32 are alternately arranged in planar view of imaging device 3 where a horizontal arrangement of first elements 31 is defined as a row and the vertical arrangement thereof is defined as a column.

Here, another embodiment of the positional relation between light source unit 2 and imaging device 3 will be described with reference to FIG. 4.

Figure 4:
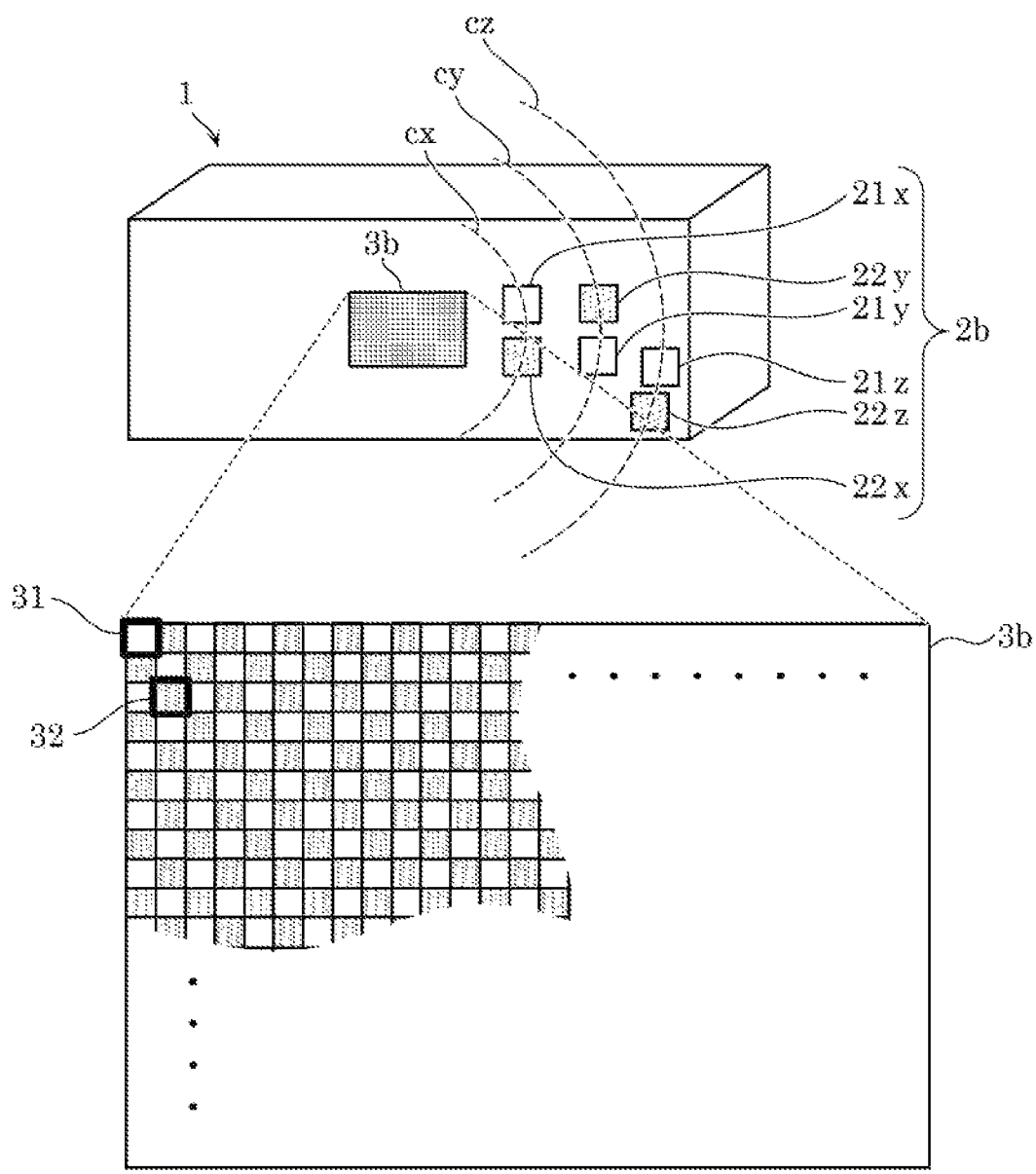
FIG. 4 is a diagram illustrating the positional relation between the light source unit and the imaging device arranged in the biological state detecting apparatus according to another embodiment.

FIG. 4 is a diagram illustrating another embodiment of the positional relation between light source unit 2b and imaging device 3b arranged in biological state detecting apparatus 1.

In FIG. 4, the upper illustration shows a surface of biological state detecting apparatus 1 including light source unit 2b and imaging device 3b in planar view. In FIG. 4, the lower illustration shows an enlarged view of imaging device 3b, where the unit elements which constitute imaging device 3b are arranged in a lattice form. In FIG. 4, the corners in the upper illustration are connected to the corresponding corners in the lower illustration with the dashed lines, respectively. In the lower illustration, the lattice surface formed of the unit elements is drawn only halfway for convenience.

Unlike the arrangement in FIG. 3, light source unit 2b has an arrangement where the light sources are concentrated on the right side of the illustration and any light source is not present on the left side. Furthermore, first light source 21x and second light source 22x are arranged in positions closer to imaging device 3b than the positions of the light sources to imaging device 3 in the example of FIG. 3. Thus, the biological state can be detected only by the pair of light sources (first light source 21x and second light source 22x), which are arranged on circle cx drawn around imaging device 3b. Moreover, first light source 21y and second light source 22y are arranged in the inverted pattern of the light sources in the example of FIG. 3. The biological state can be detected only by the pair of light sources (first light source 21y and second light source 22y), which are arranged on circle cy drawn around imaging device 3b. First light source 21z and second light source 22z are arranged in positions remoter from imaging device 3b than the positions of the light sources from imaging device 3 in the example of FIG. 3, and are concentrated in the lower portion of the illustration. The biological state can be detected only by the pair of light sources (first light source 21z and second light source 22z), which are arranged on circle cz drawn around imaging device 3b.

Unlike imaging device 3 in FIG. 3, as an example shown, imaging device 3b has an arrangement in a houndstooth-checked pattern such that first element 31 and second element 32 are alternately arranged both in the vertical direction and the horizontal direction. In this embodiment, first elements 31 and second elements 32 are arranged adjacent to each other in all the directions, i.e., the vertical and horizontal directions. In this case, light reception by individual unit elements should be separately controlled, and use of a CMOS image sensor as a solid state imaging device is assumed.

Furthermore, more details of first element 31 and second element 32 will now be described with reference to FIG. 5.

Figure 5:
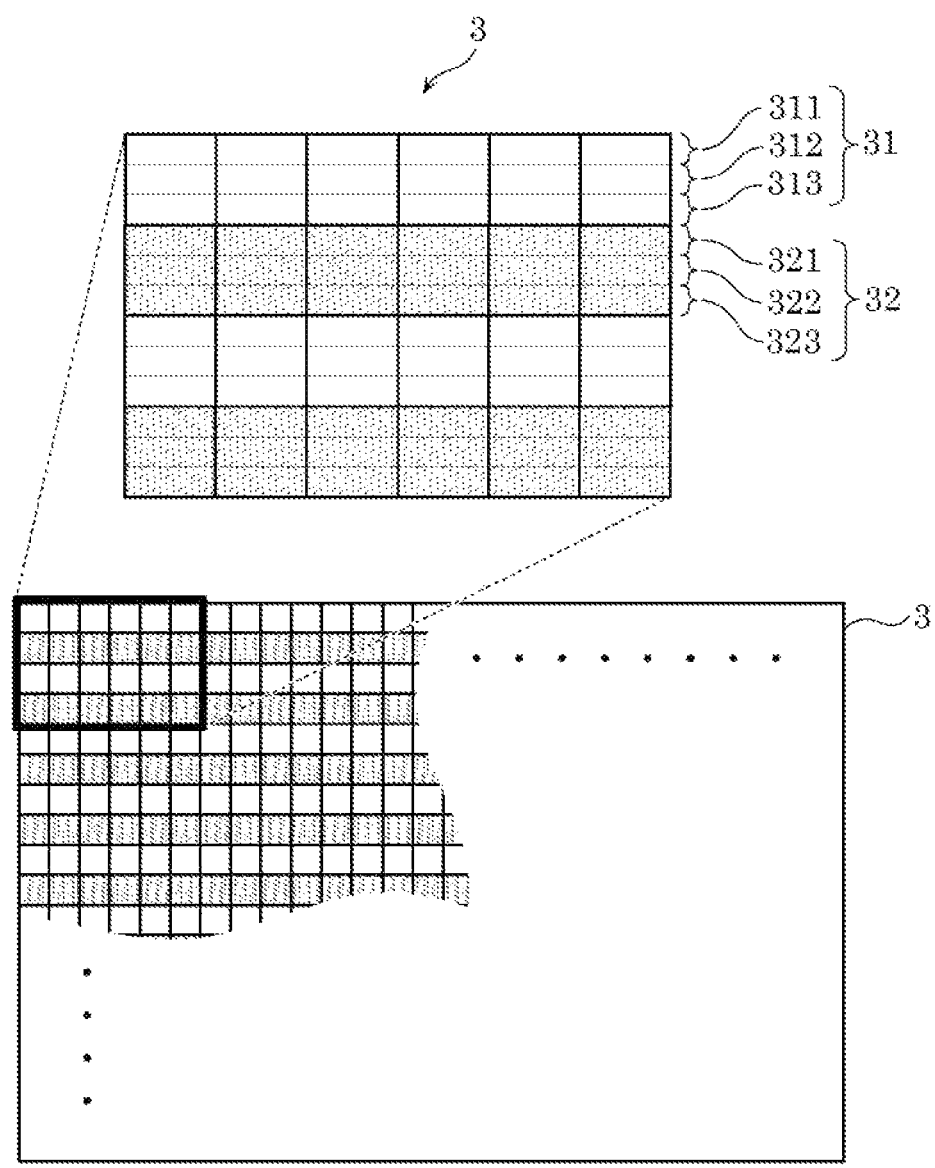
FIG. 5 is an enlarged view of unit elements which constitute the imaging device included in the biological state detecting apparatus according to the embodiment.

FIG. 5 is an enlarged view illustrating the unit elements which constitute imaging device 3 included in biological state detecting apparatus 1 according to the embodiment.

In FIG. 5, the lower illustration shows imaging device 3 identical to that shown in the lower illustration in FIG. 3, and the upper illustration shows an enlarged view of twenty-four (uppermost four rows by leftmost six columns of) unit elements in imaging device 3 shown in the lower illustration. In the present embodiment, exposure of imaging device 3 to light can be performed at several timings. In this illustration, in particular, the elements which are included in imaging device 3 and accumulate charges generated at each timing of light exposure are focused. In the lower illustration in FIG. 5, the unit elements corresponding to those shown in the upper illustration are indicated by the rectangular frame, and the corners corresponding to each other are connected by the dashed lines.

Each unit element of first element 31 further includes four elements, i.e., a first light receiving element (not illustrated in FIG. 5) which receives reflected light 21b and background light 10a to generate charges through photoelectric conversion, element 311 which accumulates the charges generated at a first light exposure timing, element 312 which accumulates the charges generated at a second light exposure timing, and element 313 which accumulates the charges generated at a third light exposure timing. Similarly, each unit element of second element 32 includes a second light receiving element, element 321, element 322, and element 323. Elements 311 to 313 in first element 31 accumulate the charges sequentially generated with emission from its corresponding first light source 21, and each output an electric signal at its light exposure timing according to the light quantity received by first element 31. Similarly, elements 321 to 323 in second element 32 accumulate the charges sequentially generated with emission from its corresponding second light source 22, and each output an electric signal at its light exposure timing according to the light quantity received by second element 32. Next, the operation of biological state detecting apparatus 1 according to the present embodiment having such a configuration will be described with reference to FIGS. 6 to 12.

First, the overall operation of biological state detecting apparatus 1 according to the present embodiment and pulse detection in state estimator 6 using images will be described with reference to FIGS. 6 and 7.

Figure 6:
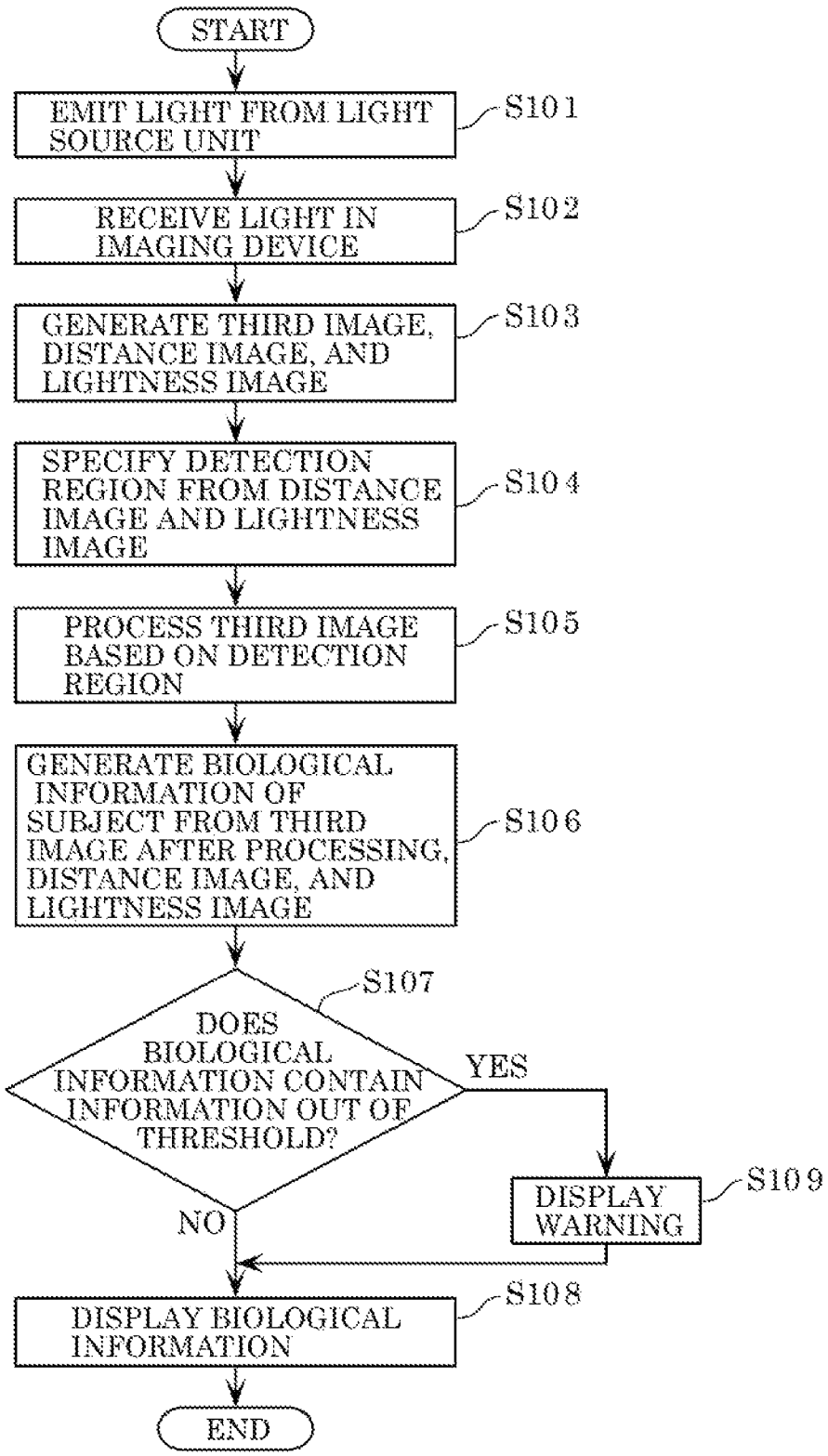
FIG. 6 is a flowchart illustrating the overall operation of the biological state detecting apparatus according to the embodiment.

FIG. 6 is a flowchart illustrating the overall operation of biological state detecting apparatus 1 (that is, the biological state detection method) according to the embodiment. FIG. 7 is a diagram illustrating specification of a detection region and pulse detection by biological state detecting apparatus 1 according to the embodiment.

Initially, a user of biological state detecting apparatus 1 installs biological state detecting apparatus 1 in a position such that person 9 as the detection target is contained within the imaging space of biological state detecting apparatus 1, and starts the operation.

Then, based in the setting value preset or that set by the user at the start of operation, biological state detecting apparatus 1 starts generating the biological information representing the biological state of person 9. Controller 4 in biological state detecting apparatus 1 initially controls first light source 21 and second light source 22 such that emission light 21a from first light source 21 and emission light 22a from second light source 22 are alternately emitted (control step S101). Emission light 21a and emission light 22a are reflected by objects (including person 9) which are present within the imaging space, and are received as reflected light 21b and reflected light 22b in first elements 31 and second elements 32, respectively (S102). The light received at this time includes background light 10a radiated from background light source 10. Arithmetic operator 5 performs arithmetic operation on the first image and the second image read from first elements 31 and second elements 32, respectively, to generate third image 37, lightness image 38, and distance image 39 (arithmetic operation step S103). Based on lightness image 38 and distance image 39 generated, detection region specifier 61 in state estimator 6 specifies detection region 62 to determine a region of third image 37 used to generate the biological information (state estimation step S104).

Figure 7:
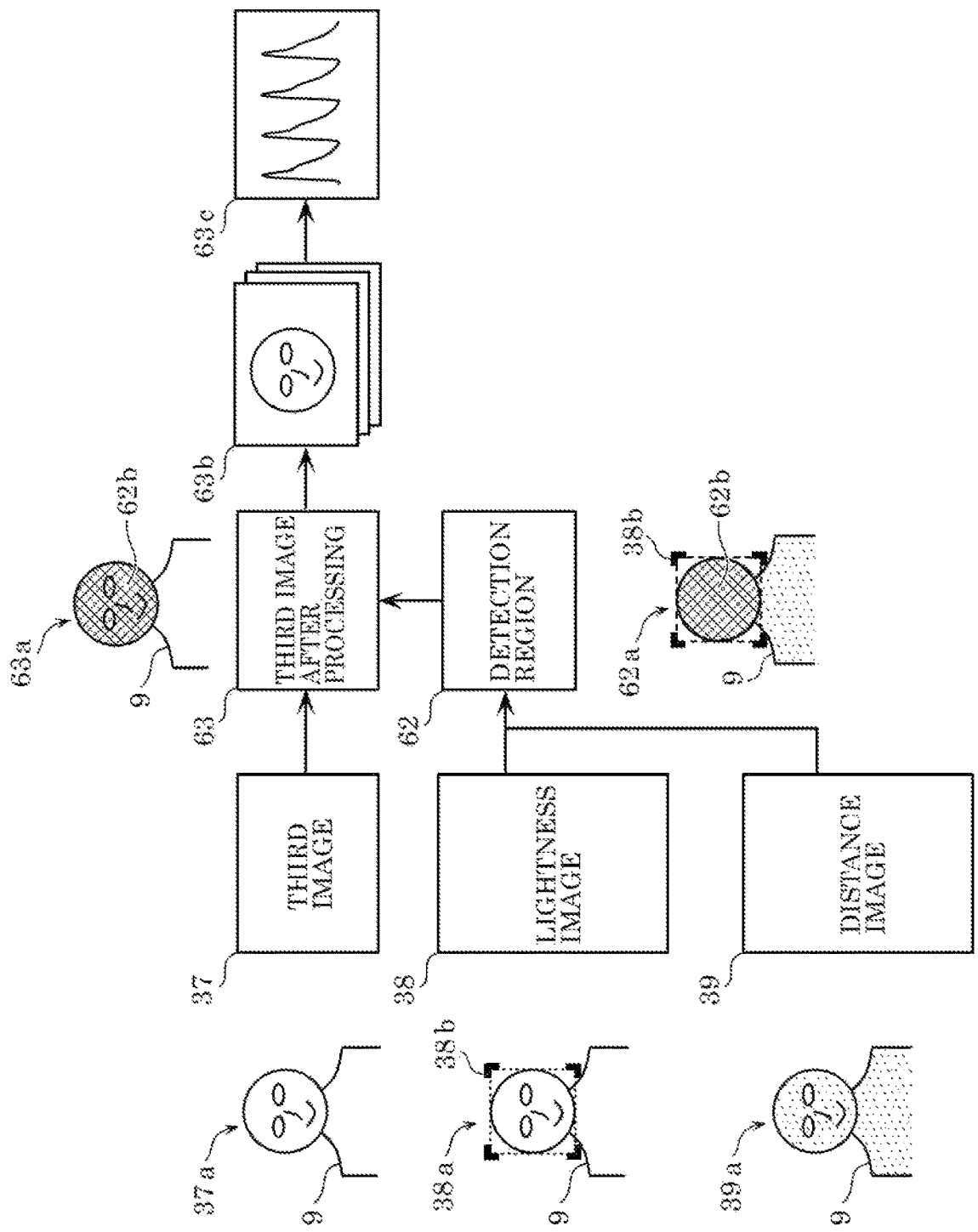
FIG. 7 is a diagram illustrating specification of the detection region and the pulse detection by the biological state detecting apparatus according to the present embodiment.

More specifically, as illustrated in FIG. 7, detection region specifier 61 included in state estimator 6 obtains lightness image 38 and distance image 39 generated by arithmetic operator 5. Here, as illustrated in image example 38a of lightness image 38 and image example 39a of distance image 39, lightness image 38 and distance image 39 are images representing the lightness and the distance, respectively, when the space containing the facial portion of person 9 is captured. In lightness image 38 obtained, detection region specifier 61 detects face detection area 38b through contour extraction of pixels located in the facial portion of person 9 and generation of the bounding rectangle. In image example 38a, face detection area 38b detected as the facial portion is exemplified where face detection area 38b is surrounded by a rectangular frame drawn with the dashed line with bolded corners.

Next, detection region specifier 61 selects pixels on distance image 39 which correspond to the pixels located in the facial portion detected on lightness image 38. The pixels located at an approximately equal distance from the central pixel of distance image 39 (in other words, in an equal distance range) are selected as detection region example 62b from the pixels corresponding to face detection area 38b selected on distance image 39. In other words, a region of distance image 39 without the background located outside the facial portion is selected as detection region example 62b. The pixels of distance image 39 corresponding to the facial portion detected in lightness image 38 have an approximately identical distance because these pixels reflect the distance to the face. Image example 62a of detection region 62 is illustrated, where face detection area 38b is overlaid on image example 39a, and of face detection area 38b, a range having approximately identical distance information is indicated as detection region example 62b.

In FIG. 6, after detection region 62 is specified, based on detection region 62 specified, state estimator 6 processes third image 37 output from arithmetic operator 5 to generate third image 63 after processing, which has only information on the portion corresponding to detection region 62 (S105).

Image example 37a of third image 37 illustrated in FIG. 7 is also an image obtained in the same frame as those of image examples 38a and 39a by capturing the space containing the facial portion of person 9. State estimator 6 overlays detection region 62, which is previously obtained in the same frame, on third image 37, and deletes the non-overlapping image information from third image 37. State estimator 6 temporarily stores the obtained third image 63 after processing in storage 7. Image example 63a of third image 63 after processing is illustrated where detection region example 62b is overlaid on image example 37a.

After generating third image 63 after processing, state estimator 6 generates biological information such as the pulse, breathing, and posture of person 9 from several frames of third image 63 after processing, lightness image 38, and distance image 39 accumulated in storage 7 (S106).

The processing to generate the biological information will now be described in detail with reference to FIG. 7 where third image 63 after processing is used as one example.

The series of processings by detection region specifier 61 described above is applied to all the frames of third image 37 obtained sequentially by arithmetic operator 5, and thereby the resulting frames of third image 63 after processing are accumulated in storage 7. The accumulated series of third image 63 after processing represents a change in third image 63 after processing against a change over time. In other words, the accumulated series of third images 63 after processing is third image moving picture 63b representing a change over time of the facial portion in third image 37.

Here, widening of the blood vessel, namely, the blood flow rate has a correlation with the amount of hemoglobin. Use of light having a wavelength highly reflective to hemoglobin results in the reflected light corresponding to the amount of hemoglobin per unit time during irradiation with light. The wavelength highly reflective to hemoglobin refers to the wavelength of the incident light barely absorbed in the body tissues and at least partially reflected by hemoglobin. Use of such reflected light enables non-invasive observation of the widening of the blood vessel. The pulse can be estimated by plotting the change over time in the widening of the blood vessel. In other words, the pulse can be non-invasively estimated using the images.

Third image moving picture 63b previously obtained is generated by plotting a change over time in the reflected light of the light having an arbitrary wavelength emitted onto the facial portion. The pulse of person 9 can be estimated by using the arbitrary wavelength as the wavelength highly reflective to hemoglobin. Thus, state estimator 6 estimates the pulse of person 9 through analysis of third image moving picture 63b, and generates diagram 63c of the estimated pulse as well as the estimated pulse value as the biological information.

State estimator 6 also analyzes lightness image 38 and distance image 39 as a lightness image moving picture and a distance image moving picture, respectively, to generate a variety of pieces of biological information.

In FIG. 6, after generating the biological information, state estimator 6 determines whether the generated biological information contains any biological information indicating a value out of the preset reference value (S107). When such biological information is not present (No in S107), a list or part of the biological information currently obtained is displayed on display 8 (S108). In contrast, when the biological information indicating a value out of the present reference value is present (Yes in S107), state estimator 6 displays a warning on display 8 to notify the user of the abnormal value (S109). Subsequently, state estimator 6 displays a list or part of the biological information including the information indicating the abnormal value (S108).

Next, individual operations in the overall operation of biological state detecting apparatus 1 illustrated in FIGS. 6 and 7 will be described in more detail.

First, processing in emission from light source unit 2 and light reception by imaging device 3 will be described in detail with reference to FIG. 8. The description here corresponds to steps S101 and S102 in the flowchart illustrated in FIG. 6.

Figure 8:
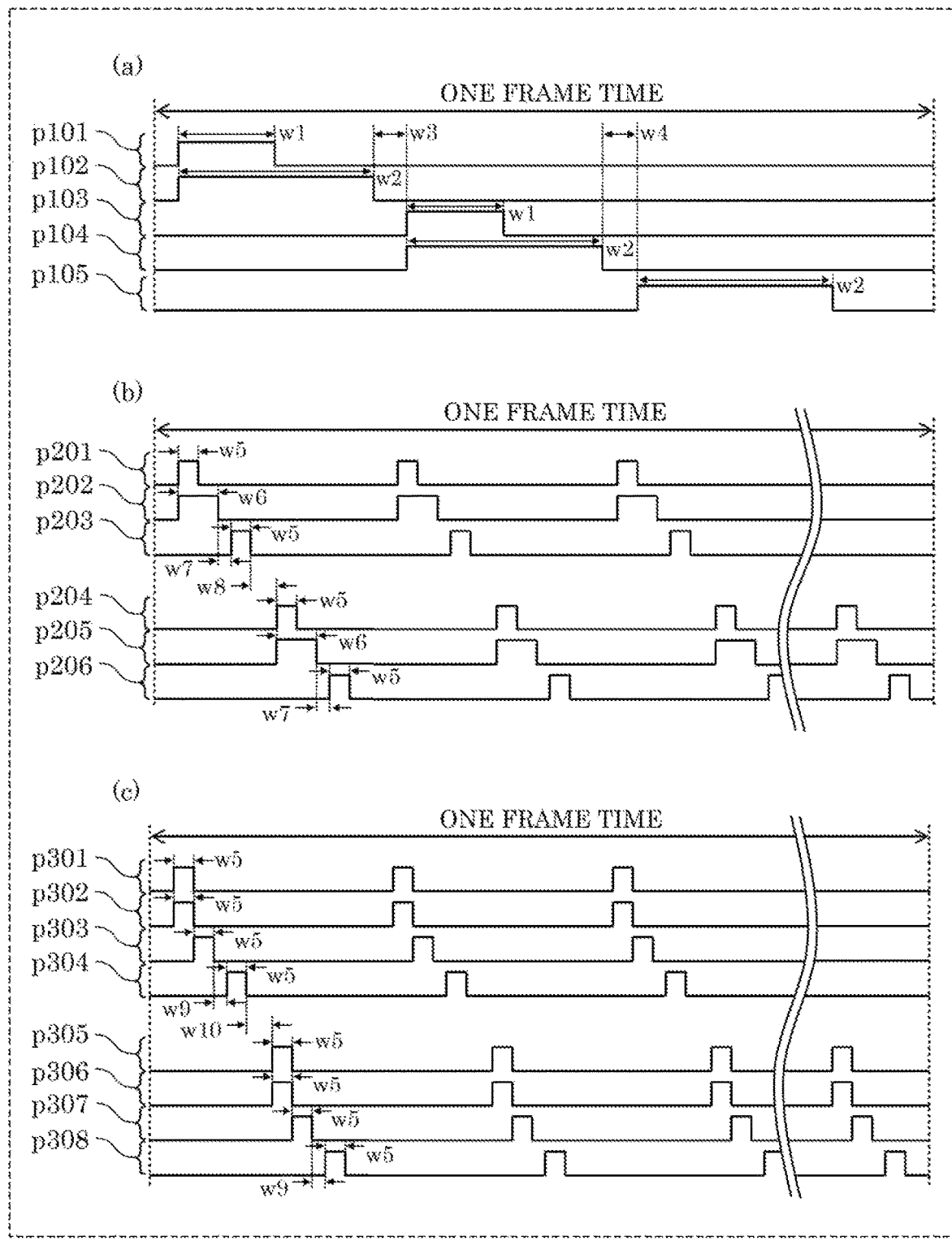
FIG. 8 is a timing chart of the control of the light source unit and the imaging device included in the biological state detecting apparatus according to the embodiment.

FIG. 8 is a timing chart illustrating the control of light source unit 2 and imaging device 3 included in biological state detecting apparatus 1 according to the embodiment.

In FIG. 8, the abscissa represents a lapse of time and the ordinate represents ON and OFF of emission from the light source or light reception by imaging device 3. Here, the upper side of the ordinate indicates ON control and the lower side of the ordinate indicates OFF control. Because each element receives light at two or three different light exposure timings, the operation will be described using elements 311 and 321, elements 312 and 322, and elements 313 and 323 illustrated in FIG. 5. When first element 31 and second element 32 receive light at two different light exposure timings, first element 31 and second element 32 may have a configuration without elements 312 and 322, respectively.

(a) of FIG. 8 is a timing chart illustrating the one-time control within one frame time for emission from first light source 21 (first timing chart p101), light reception in first element 31 (second timing chart p102), emission from second light source 22 (third timing chart p103), light reception in second element 32 (fourth timing chart p104), and reception of background light 10a in first element 31 and second element 32 (fifth timing chart p105). Because light reception is performed at two different timings here, the operation will be described using elements 311 and 321 and elements 313 and 323 in FIG. 5.

First, in first timing chart p101 indicating emission from first light source 21, emission from first light source 21 is started, and is stopped after a time of first pulse width w1 has passed.

In second timing chart p102 indicating light reception in first element 31, accumulation of charge in element 311 is started simultaneously with the start of emission from first light source 21, and is stopped after a time of second pulse width w2 has passed, thus obtaining an electric signal corresponding to a first image.

In third timing chart p103 indicating emission from second light source 22, emission from second light source 22 is started after a time of first interval w3 has passed from the stop of accumulation of charge in element 311, and is stopped after a time of first pulse width w1 has passed.

In fourth timing chart p104 indicating light reception in second element 32, accumulation of charge in element 321 is started simultaneously with the start of emission from second light source 22, and is stopped after a time of second pulse width w2 has passed, thus obtaining an electric signal corresponding to a second image.

Furthermore, in fifth timing chart p105 indicating reception of background light 10a in first element 31 and second element 32, accumulation of charges in elements 313 and 323 is started after a time of second interval w4 has passed from the stop of accumulation of charge in element 321, and is stopped after a time of second pulse width w2 has passed, thus obtaining an electric signal corresponding to a fourth image.

The above operation is defined as one set of control, and one set is performed within one frame time. In this timing chart, the fourth image can be obtained in addition to the first image and the second image captured at two wavelengths. Thus, arithmetic operator 5 can generate a first subtraction image and a second subtraction image by removing the background light from the first and second images, respectively.

(b) of FIG. 8 is a chart illustrating the control where the one set of control illustrated in (a) of FIG. 8 is divided into several times and performed within one frame time. Furthermore, in (b) of FIG. 8, first element 31 receives background light 10a (eighth timing chart p203) immediately after emission from first light source 21 (sixth timing chart p201) and light reception in first element 31 (seventh timing chart p202). Subsequently, second element 32 receives background light 10a (eleventh timing chart p206) immediately after emission from second light source 22 (ninth timing chart p204) and light reception in second element 32 (tenth timing chart p205). Because light is received at two different timings here, the operation will be described using elements 311 and 321 and elements 313 and 323 in FIG. 5.

Initially, in sixth timing chart p201 indicating emission from first light source 21, emission from first light source 21 is started, and is stopped after a time of third pulse width w5 has passed.

In seventh timing chart p202 indicating light reception in first element 31, accumulation of charge in element 311 is started simultaneously with the emission from first light source 21, and is stopped after a time of fourth pulse width w6 has passed.

Subsequently, in eight timing chart p203 indicating reception of background light 10a in first element 31, accumulation of charge in element 313 is started after a time of third interval w7 has passed from the stop of accumulation of charge in element 311, and is stopped after a time of third pulse width w5 has passed.

In ninth timing chart p204 indicating emission from second light source 22, emission from second light source 22 is started after a time of fourth interval w8 has passed from the stop of accumulation of charge in element 313, and is stopped after a time of third pulse width w5 has passed.

In tenth timing chart p205 indicating light reception in second element 32, accumulation of charge in element 321 is started simultaneously with the emission from second light source 22, and is stopped after a time of fourth pulse width w6 has passed.

Subsequently, in eleventh timing chart p206 indicating reception of background light 10a in second element 32, accumulation of charge in element 323 is started after a time of third interval w7 has passed from the stop of accumulation of charge in element 321, and is stopped after a time of third pulse width w5 has passed.

The above operation is defined as one set of control, and several sets of emission and light reception are repeated within one frame time to integrate the charges accumulated in the elements. In this timing chart, in addition to the first image and the second image captured at two wavelengths, respectively, the fourth images can also be obtained within one frame time. Thus, arithmetic operator 5 can generate a first subtraction image and a second subtraction image by removing the background light from the first and second images, respectively. In this timing chart, the emission and the light reception are performed several times, and thus the change generated within the one frame time can be more accurately captured. Moreover, the difference between the timing of charge accumulation in element 311 and that in element 313 is identical to the difference between the timing of charge accumulation in element 321 and that in element 323, thus reducing the difference in image capturing between the two light sources.

Furthermore, in the operation illustrated in (c) of FIG. 8, in addition to the operation illustrated in (b) of FIG. 8, the timing of light reception in each of first element 31 and second element 32 is divided into two timings on the time axis to enable capturing by a time of flight (TOF) method. Here, light is received at three different timings, and thus the operation will be described using elements 311 and 321, elements 312 and 322, and elements 313 and 323 in FIG. 5.

Initially, in twelfth timing chart p301 indicating emission of first light source 21, emission from first light source 21 is started, and is stopped after a time of third pulse width w5 has passed.

In thirteenth timing chart p302 indicating accumulation of charge in element 311, accumulation of charge in element 311 is started simultaneously with the start of the emission from first light source 21, and is stopped after a time of third pulse width w5 has passed.

In fourteenth timing chart p303 indicating accumulation of charge in element 312, accumulation of charge in element 312 is started simultaneously with the stop of the accumulation of charge in element 311, and is stopped after a time of third pulse width w5 has passed.

Subsequently, in fifteenth timing chart p304 indicating reception of background light 10a in first element 31, accumulation of charge in element 313 is started after a time of fifth interval w9 has passed from the stop of the accumulation of charge in element 312, and is stopped after a time of third pulse width w5 has passed.

In sixteenth timing chart p305 indicating emission from second light source 22, emission from second light source 22 is started after a time of sixth interval w10 has passed from the stop of the accumulation of charge in element 313, and is stopped after a time of third pulse width w5 has passed.

In seventeenth timing chart p306 indicating light reception in element 321, accumulation of charge in element 321 is started simultaneously with the start of emission from second light source 22, and is stopped after a time of third pulse width w5 has passed.

In eighteenth timing chart p307 indicating accumulation of charge in element 322, accumulation of charge in element 322 is started simultaneously with the stop of the accumulation of charge in element 321, and is stopped after a time of third pulse width w5 has passed.

Subsequently, in nineteenth timing chart p308 indicating reception of background light 10a in second element 32, accumulation of charge in element 323 is started after a time of fifth interval w9 has passed from the stop of the accumulation of charge in element 322, and is stopped after a time of third pulse width w5 has passed.

The above operation is defined as one set of control, and several sets of emission and light reception are repeated within one frame time to integrate the accumulated charges in the elements, respectively. In this timing chart, analysis by the TOF method can be performed, thus enabling calculation of the distance between imaging device 3 and an object present within the imaging space.

To be noted, the emission and the light reception are performed according to (c) of FIG. 8 in the description of the present embodiment, and thus, arithmetic operator 5 can obtain the distance image by the TOF method.

Here, the method of calculating the distance by the TOF method will be described using the following equation (1):

[Expression 1]

$$L_w = \frac{cT_w}{2} \cdot \frac{t2 - t0}{t1 + t2 - 2t0} \quad (1)$$

Equation (1) is a computational expression for calculating the distance at a first wavelength from an object present within the imaging space to imaging device 3. Here, $L_W$ represents the distance from the object present within the imaging space to imaging device 3, c represents the light velocity, Tw represents the pulse width of the light at the first wavelength to be emitted, t1 represents the quantity of received light at a first light exposure timing, t2 represents the quantity of received light at a second light exposure timing, and t0 represents the quantity of received light at a third light exposure timing. More specifically, $3.00 \times 10^8$ is substituted for c, third pulse width w5 for Tw, the charge amount of element 311 for t1, the charge amount of element 312 for t2, and the charge amount of element 313 for t0 to calculate the distance.

The distance at a second wavelength from the object present within the imaging space to imaging device 3 is also calculated using the same equation. More specifically, $3.00 \times 10^8$ is substituted for c, third pulse width w5 for Tw, the charge amount of element 321 for t1, the charge amount of element 322 for t2, and the charge amount of element 323 for t0 to calculate the distance.

Next, the processing to generate the biological information from the electric signals accumulated in imaging device 3 as above will be described with reference to FIG. 9. The description here corresponds to steps S103 to S108 in the flowchart illustrated in FIG. 6.

Figure 9:
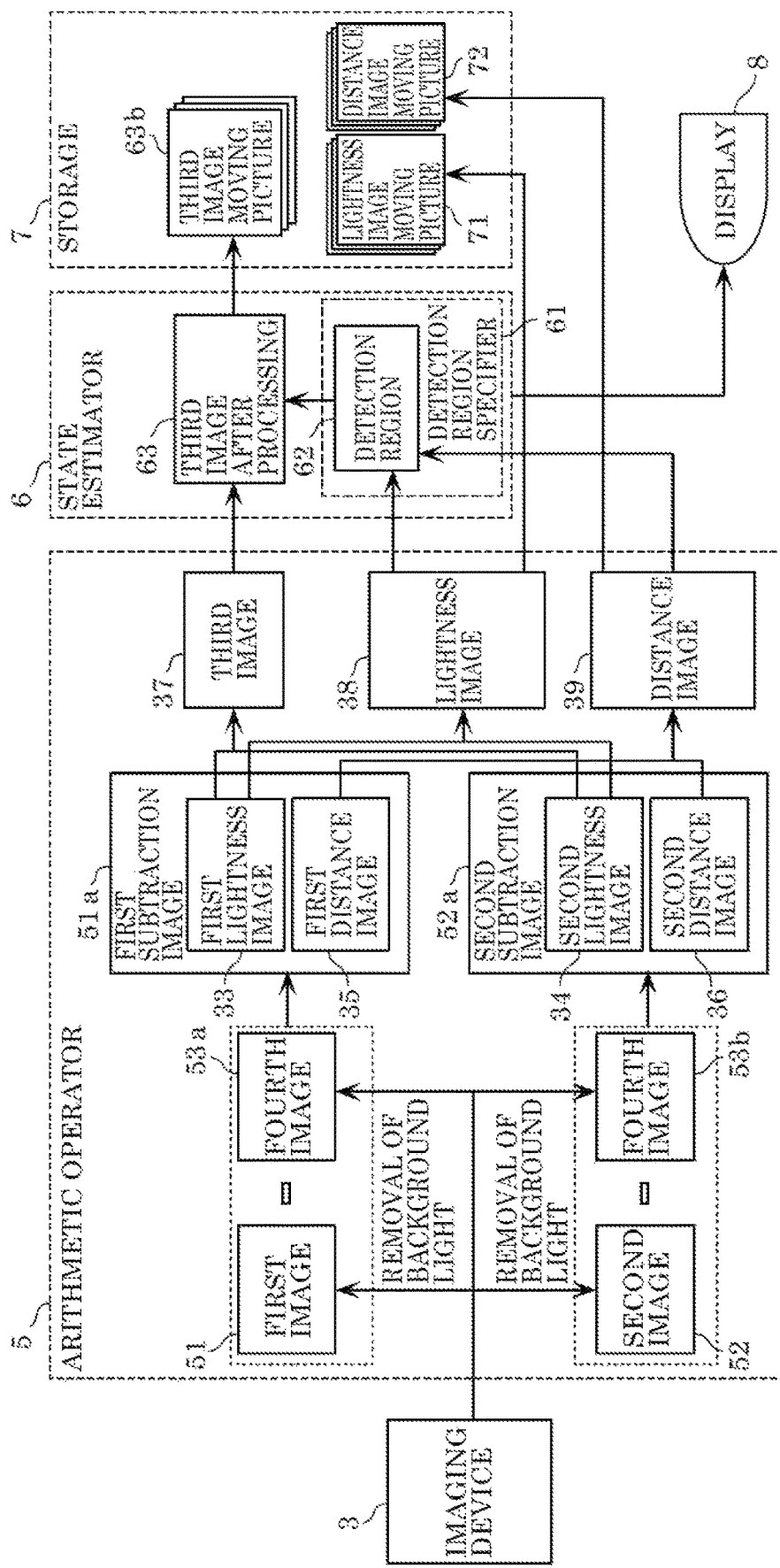
FIG. 9 is a diagram illustrating image processing by the biological state detecting apparatus according to the embodiment.

FIG. 9 is a diagram illustrating the image processing by biological state detecting apparatus 1 according to the embodiment.

FIG. 9 illustrates a flow of a series of image processing where arithmetic operator 5 reads out an image from imaging device 3 to process it, and state estimator 6 further processes the image processed by arithmetic operator 5 to estimate the biological state. FIG. 9 also illustrates the image processing in state estimator 6 where the image is temporarily stored in storage 7 and the result of estimation is output to display 8.

Initially, arithmetic operator 5 reads out the image information obtained in imaging device 3, and generates three types of image information by processing the image information through subtraction or synthesis. Specifically, arithmetic operator 5 reads out first image 51 and second image 52 from first elements 31 and second elements 32, respectively, in imaging device 3, first image 51 being obtained during emission from the light source having the first wavelength, second image 52 being obtained during emission from the light source having the second wavelength. At the same time, from imaging device 3, arithmetic operator 5 reads out fourth images 53a and 53b captured by first elements 31 and second elements 32, respectively, under an environment having only background light 10a without any irradiation from the light sources. Arithmetic operator 5 removes background light 10a by taking the difference between first image 51 and fourth image 53a read out from imaging device 3, and outputs first subtraction image 51a. Similarly, arithmetic operator 5 removes background light 10a by taking the difference between second image 52 and fourth image 53b read out from imaging device 3, and outputs second subtraction image 52a.

Here, first subtraction image 51a contains first lightness image 33 and first distance image 35. Second subtraction image 52a contains second lightness image 34 and second distance image 36. Arithmetic operator 5 generates third image 37 for generation of the biological information by taking the difference between first lightness image 33 and second lightness image 34. Arithmetic operator 5 generates lightness image 38 used for specification of detection region 62 by synthesizing first lightness image 33 and second lightness image 34. Furthermore, arithmetic operator 5 generates distance image 39 used for specification of detection region 62 by synthesizing first distance image 35 and second distance image 36.

Arithmetic operator 5 further stores lightness image 38 and distance image 39 generated above in storage 7. As described above, arithmetic operator 5 stores and accumulates sequentially obtained frames of the images in storage 7 to generate lightness image moving picture 71 and distance image moving picture 72, respectively.

Next, using lightness image 38 and distance image 39 generated by arithmetic operator 5, detection region specifier 61 in state estimator 6 specifies detection region 62 used to detect the biological information.

Using detection region 62 for third image 37 generated by arithmetic operator 5, state estimator 6 generates third image 63 after processing, which is the image information containing only a portion corresponding to detection region 62, and stores third image 63 after processing in storage 7. State estimator 6 applies the above processing to the sequentially obtained frames of third image 63 after processing to generate third image moving picture 63b. State estimator 6 generates the biological information of person 9 using lightness image moving picture 71, distance image moving picture 72, and third image moving picture 63b stored in storage 7. State estimator 6 causes display 8 to display the biological information thus generated.

Next, the processing of the images performed by arithmetic operator 5 according to the present embodiment will be described in more detail with reference to FIG. 10. The description here corresponds to step S103 in the flowchart illustrated in FIG. 6.

Figure 10:
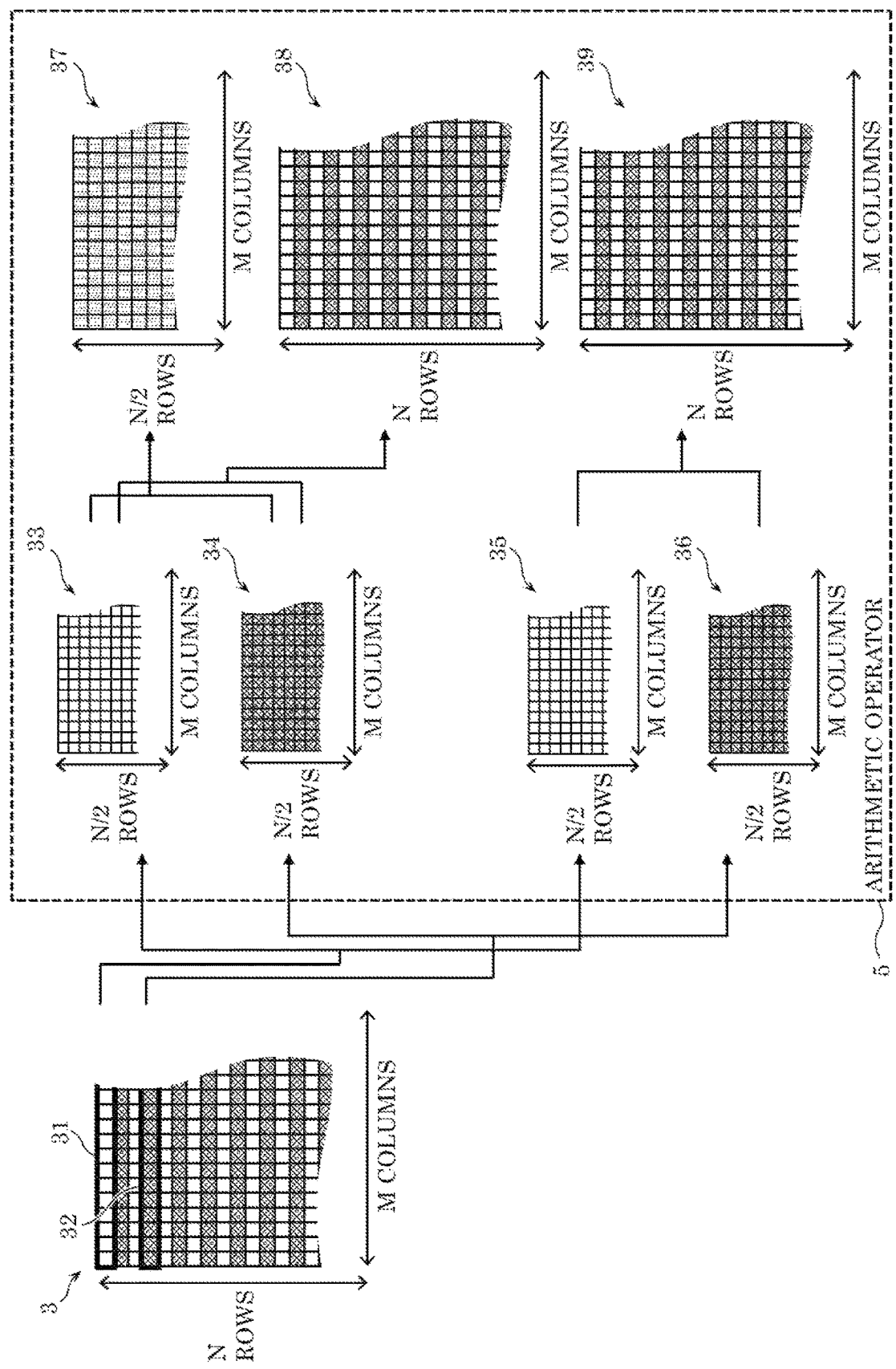
FIG. 10 is a diagram illustrating image processing by the arithmetic operator included in the biological state detecting apparatus according to the embodiment.

FIG. 10 is a diagram illustrating the image processing by arithmetic operator 5 included in biological state detecting apparatus 1 according to the embodiment.

FIG. 10 illustrates imaging device 3 and the image information where the pixels corresponding to the unit elements in imaging device 3 are aligned according to the arrangement of the unit elements. For convenience, the right end and the lower ends are not illustrated in imaging device 3 and the image information. Imaging device 3 is configured of the unit elements arranged in N rows in the vertical direction and M columns in the horizontal direction (where N and M are each an integer of 2 or more), where first element 31 and second element 32 are alternately arranged in the horizontal direction such that first elements 31 are located in the odd columns and second elements 32 are located in the even columns.

Here, first image 51 captured by first element 31 contains the lightness information indicating the quantity of the light received by the pixels which constitute first image 51, and the distance information indicating the distance between an object within the imaging space and imaging device 3, which is obtained by the TOF method. Similarly, second image 52 captured by second element 32 also contains the corresponding lightness information and the corresponding distance information. In FIG. 10, the image indicating the lightness information in first image 51 is represented as first lightness image 33 and the image indicating the distance information is represented as first distance image 35. The image indicating the lightness information in second image 52 is represented as second lightness image 34 and the image indicating the distance information is represented as second distance image 36. Furthermore, FIG. 10 also illustrates third image 37, lightness image 38, and distance image 39 obtained through processing in arithmetic operator 5.

After the capturing by imaging device 3 is completed, arithmetic operator 5 reads out the electric signals indicating the image information, which are accumulated in elements 311 and 321 and elements 312 and 322 in imaging device 3. At this time, first image 51 is obtained by processing to extract the quantity of received light in first elements 31 arranged in the odd columns, and second image 52 is obtained by processing to extract the quantity of received light in second elements 32 arranged in the even columns. In other words, two pieces of image information of N/2 rows by M columns of pixels (where the amount of information is half in the vertical direction) are generated from N rows by M columns of unit elements arranged on the original imaging device 3. Arithmetic operator 5 also reads out fourth images 53a and 53b from elements 313 and 323, respectively, the fourth images being captured under an environment where only background light 10a is radiated. Arithmetic operator 5 initially subtracts fourth images 53a and 53b, which are read out from the corresponding elements, from first image 51 and second image 52, respectively, to generate first subtraction image 51a and second subtraction image 52a from which the received light due to radiation of background light 10a is removed.

Here, at the same time when arithmetic operator 5 subtracts fourth images 53a and 53b from first image 51 and second image 52, respectively, arithmetic operator 5 individually performs arithmetic operation on the lightness information and the distance information contained in the pixels to obtain first lightness image 33, first distance image 35, second lightness image 34, and second distance image 36.

Specifically, arithmetic operator 5 adds the charge amounts of elements 311 and 321 to those of elements 312 and 322, subtracts the charge amounts twice those of elements 313 and 323 from the results, and aligns the pixels according to the arrangement on imaging device to obtain first lightness image 33 and second lightness image 34, respectively. Arithmetic operator 5 performs an arithmetic operation on the charge amounts of elements 311 and 321, those of elements 312 and 322, and those of elements 313 and 323 using equation (1) above to obtain first distance image 35 and second distance image 36, respectively.

Through the processing described above, arithmetic operator 5 obtains the four pieces of image information (first lightness image 33, second lightness image 34, first distance image 35, and second distance image 36) from the electric signals accumulated in imaging device 3 within one frame time.

Arithmetic operator 5 further computes the difference between first lightness image 33 and second lightness image 34 to obtain third image 37. In the computation of third image 37, the difference is calculated for each pair of the pixels located in the same positions in first lightness image 33 and second lightness image 34. For this reason, while the values of the pixels change, the number of pixels in the image does not change before and after the processing, obtaining the image information of N/2 rows by M columns of pixels.

Although arithmetic operator 5 generates third image 37 from the difference between first lightness image 33 and second lightness image 34 in the present embodiment, third image 37 may be generated from the ratio of these two images.

Arithmetic operator 5 also synthesizes first lightness image 33 and second lightness image 34 to obtain lightness image 38. Specifically, the first row of second lightness image 35 is inserted under the first row of first lightness image 33, and the second row of second lightness image 34 is inserted under the second row of first lightness image 33. This processing is repeated to the last row of the N/2 rows. Thus, synthesis is performed to reproduce the arrangement positions of the unit elements in the original imaging device 3. While the values of the pixels do not change in the image obtained through this processing, the number of pixels in the image changes before and after the processing, thus obtaining the image information of N rows by M columns of pixels.

Here, first lightness image 33 and second lightness image 34 are images obtained by the light beams emitted at different wavelengths, respectively. The resulting first lightness image 33 and second lightness image 34 may have a difference in lightness (that is, luminance) caused by the difference in reflectance of the object within the imaging space caused by the two wavelengths or the difference in sensitivity between first element 31 and second element 32. Thus, a processing to correct the difference in light quantity may be performed simultaneously with the synthesis of lightness image 38. Specifically, a referential pixel is determined in each of the resulting lightness image 33 and second lightness image 34, and for the referential pixels in the resulting images, the ratio of the quantity of received light in one image obtained with a smaller light quantity to that in the other image obtained with a larger light quantity is calculated. For the next synthesis, the luminance of the light emitted from the light source used to capture the image obtained with a larger light quantity is adjusted using the ratio of the quantity of received light such that the quantities of light to be received by the referential pixels are identical in the capturing of the next frame. Alternatively, for all the pixels on the image obtained with a larger light quantity, the luminance may be corrected on the image information using the ratio of the quantity of received light such that the quantities of light to be received by the pixels as the reference are identical in the resulting first and second lightness images, and the corrected lightness images may be used in synthesis.

Arithmetic operator 5 also synthesizes first distance image 35 and second distance image 36 to obtain distance image 39. Specifically, the first row of second distance image 36 is inserted under the first row of first distance image 35, and the second row of second distance image 36 is inserted under the second row of first distance image 35. This processing is repeated to the last row of the N/2 rows. Thus, synthesis is performed to reproduce the arrangement positions of the unit elements in the original imaging device 3. While the values of the pixels do not change in the image obtained through this processing, the number of pixels in the image changes before and after the processing, thus obtaining the image information of N rows by M columns of pixels.

Third image 37, lightness image 38, and distance image 39 obtained as above have N/2 rows of pixels, N rows of pixels, and N rows of pixels in the vertical direction, respectively. For this reason, a processing to double the number of pixels of third image 37 in the vertical direction is performed to compare these images at the same time. Alternatively, the numbers of pixels of lightness image 38 and distance image 39 in the vertical direction may each be reduced to ½.

Furthermore, the processing by state estimator 6 according to the present embodiment will be described with reference to FIG. 11. The description here corresponds to steps S104 to S109 in the flowchart illustrated in FIG. 6. As one example of a display of the warning, the operation of biological state detecting apparatus 1 when detecting the drowsiness information will also be described with reference to FIG. 12.

FIG. 11 is a flowchart illustrating the overall operation of state estimator 6 included in biological state detecting apparatus 1 according to the embodiment.

As described in FIG. 6, detection region specifier 61 in state estimator 6 initially obtains lightness image 38 and distance image 39 generated by arithmetic operator 5. From the image information, detection region specifier 61 in state estimator 6 performs the image processing on distance image 39 and lightness image 38 to specify detection region 62 for limiting the region used in pulse detection (S201).

Subsequently, state estimator 6 obtains third image 37 generated by arithmetic operator 5, and processes third image 37 based on detection region 62 (S202). More specifically, state estimator 6 deletes the image information out of detection region 62 in third image 37 to generate third image 63 after processing having the information of only detection region 62.

State estimator 6 further stores third image 63 after processing in storage 7, and performs the same processing to generate and accumulate several frames of third image 63 after processing. The accumulated third images 63 after processing are formed into third image moving picture 63b indicating a change over time in the image information of the facial portion of person 9 located within the region of detection region 62. State estimator 6 estimates the pulse as the biological information of person 9 through analysis of third image moving picture 63b (S203), and generates diagram 63c of the estimated pulse.

State estimator 6 analyzes distance image moving picture 72, which is accumulated distance images 39 in storage 7 representing a change over time of distance image 39, to generate the biological information of person 9, that is, posture information, behavior information, and action information (S204).

State estimator 6 further analyzes lightness image moving picture 71, which is accumulated lightness images 38 in storage 7 representing a change over time of lightness image 38, to generate the biological information of person 9, that is, eye movement information, blinking information, face orientation information, breathing information (S205).

Based on the biological information obtained as above, state estimator 6 determines whether the information indicating the drowsiness of person 9 is contained (S206). For example, state estimator 6 detects the drowsiness of person 9 by comprehensively determining detection of a pulse characteristic of the drowsiness, long-term continuation of the same posture, an increase in blinking, and downward face orientation. When detecting the drowsiness of person 9, state estimator 6 displays a warning indicating the detection of the drowsiness on display 8 (S211).

Here, FIG. 12 is a diagram illustrating one example of a display of the warning in biological state detecting apparatus 1 according to the embodiment installed in an automobile.

FIG. 12 illustrates a steering section in the view field of person 9, who is the driver of the automobile. In this example, steering wheel 100, instrument panel 101, and biological state detecting apparatus 1 are in the view field of person 9, and biological state detecting apparatus 1 has already started the operation.

Biological state detecting apparatus 1 emits light beams having different wavelengths from light source unit 2 toward person 9 as the driver and the detection target for the biological information. Emission light 21a and emission light 22a are reflected by person 9, pass through lens 3c as reflected light 21b and reflected light 22b, and reach imaging device 3. In the example illustrated in FIG. 12, the information indicating the drowsiness of the driver is detected from the captured image, and a warning to notify that the drowsiness is detected is displayed on display 8 by state estimator 6.

In the flowchart illustrated in FIG. 11, when state estimator 6 does not detect drowsiness (No in S206) or after state estimator 6 displays the warning indicating the detection of the drowsiness (S211), based on the obtained biological information, state estimator 6 determines whether the information indicating the carelessness of person 9 is contained (S207). For example, state estimator 6 detects the carelessness of person 9 by comprehensively determining that person 9 has been doing the same movement for a long time, that a pulse characteristic of carelessness is detected, and that the frequency of eye movements is changed compared to that in the normal condition. When detecting the carelessness of person 9, state estimator 6 displays a warning indicating the detection of the carelessness on display 8 (S212).

When state estimator 6 does not detect carelessness (No in S207) or after state estimator 6 displays the warning indicating the detection of the carelessness (S212), based on the obtained biological information, state estimator determines whether the information indicating the irritation of person 9 is contained (S208). For example, state estimator 6 detects the irritation of person 9 by comprehensively determining that a pulse characteristic of the irritation is detected, that the speed of the eye movement is changed compared to that in the normal condition, that the number of breaths is increased, and that the action characteristic of the irritation is detected. When detecting the irritation of person 9, state estimator 6 displays a warning indicating the detection of the irritation on display 8 (S213).

When state estimator 6 does not detect the irritation (No in S208) or after state estimator 6 displays the warning indicating the detection of the irritation (S213), state estimator 6 determines whether the obtained biological information contains an abnormal value (S209). For example, state estimator 6 detects abnormal values of the pulse, the number of breaths, and the blood pressure, as well as one or more of abnormal values of long-term closing of eyes and long-term continuation of a sleeping position. When detecting any abnormal value of the biological information, state estimator 6 displays a warning indicating the detection of the abnormal value on display 8 (S214).

When state estimator 6 does not detect any abnormal value of the biological information (No in S209) or after state estimator 6 displays the warning indicating the detection of the abnormal value (S214), state estimator 6 displays all or part of the biological information currently obtained on display 8 (S210).

To determine whether to display the warning based on the biological information above, each biological information is compared to its predetermined threshold. Besides, the previous biological information of person 9 may be stored in storage 7 as the previous data, and the current data may be compared to the maximum value, the minimum value, and the average of the previous data. At that time, person 9 may be identified based on the characteristics of the facial portion (such as the contour of the face, the sizes of the facial parts such as the eye, the nose, and the mouth, the relative positions of at least two or more facial parts, the iris, and wrinkles) in lightness image 38, and the previous data may be called out based on the identified information. Alternatively, when the previous data of person 9 is not present, the information for identifying person 9 and the biological information may be newly stored in storage 7.

Thus, biological state detecting apparatus 1 according to the present embodiment includes first light source 21 which emits light having a first wavelength; second light source 22 which emits light having a second wavelength different from the first wavelength; imaging device 3 including a plurality of elements which receive reflected light 21b of the light emitted from first light source 21 and reflected light 22b of the light emitted from second light source 22, the light emitted from first light source 21 and the light emitted from second light source 22 being reflected by person 9; controller 4 which controls first light source 21 and second light source 22 such that first light source 21 and second light source 22 alternately emit the light; arithmetic operator 5 which generates third image 37 by reading out first image 51 and second image 52 from imaging device 3, and performing an arithmetic operation on first image 51 and second image 52, first image 51 being obtained through reception of reflected light 21b of the light emitted from first light source 21, second image 52 being obtained through reception of reflected light 22b of the light emitted from second light source 22; and state estimator 6 which generates the biological information of person 9 based on third image 37 generated by arithmetic operator 5. Arithmetic operator 5 further generates distance image 39 based on at least one of first image 51 or second image 52.

Biological state detecting apparatus 1 according to the present embodiment having such a configuration can estimate the pulse as biological information, and can obtain the information on the posture, the behavior, and the action based on distance image 39. More specifically, the posture, the behavior, and the action can be estimated through analysis of the change over time in the position of person 9 (detection target for the biological information) within the imaging space, the change over time being represented by distance image moving picture 72 of distance images 39 accumulated in storage 7. Accordingly, the biological state detecting apparatus having such a configuration can generate a larger amount of biological information than that in the related art while using images.

Moreover, arithmetic operator 5 may generate distance image 39 by synthesizing first image 51 and second image 52. Thereby, distance image 39 can be generated using first image 51 and second image 52 obtained for estimation of the pulse. As a result, distance image 39 can be generated without newly capturing any image.

Moreover, arithmetic operator 5 may read out first image 51 and second image 52 from imaging device 3, and may generate distance image 39 by synthesizing first image 51 and second image 52 read out, to reproduce arrangement positions of first elements 31 and second elements 32 in imaging device 3 where first elements 31 correspond to first image 51 and second elements 32 correspond to second image 52. Thereby, distance image 39 is generated as one image according to the arrangement of the unit elements on imaging device 3 from the elements divided into two as two images for estimation of the pulse. Thus, detection region 62 can be more accurately specified using distance image 39 having high resolution.

Moreover, arithmetic operator 5 may generate distance image 39 by a time of flight method. Thereby, distance image 39 can be generated by only one imaging device 3 included in the biological state detecting apparatus, resulting in a size reduction in the whole configuration of the apparatus.

Moreover, state estimator 6 may include detection region specifier 61 which specifies detection region 62 in third image 37, which is a region used to generate the biological information, and may generate the biological information using detection region 62 specified by detection region specifier 61. At this time, for example, when it is determined that the skin is covered with a pair of glasses, a mask, or a hat and not seen from imaging device 3, detection region specifier 61 may specify detection region 62 to exclude the region where the skin is covered. Alternatively, detection region specifier 61 may specify detection region 62 to exclude the regions having a lightness different from that of the skin, such as the eyes and the oral cavity. Thereby, more appropriate pixels to generation of the biological information can be selected from the image, generating more precise biological information.

Moreover, detection region specifier 61 may specify detection region 62 using distance image 39. Thereby, the target portion of person 9 to be specified as detection region 62 can be narrowed using the distance, enabling efficient specification of the detection region.

Moreover, arithmetic operator 5 may further generate lightness image 38 based on at least one of first image 51 or second image 52, and detection region specifier 61 may specify detection region 62 using distance image 39 and lightness image 38. Thereby, the information of eye movement, blinking, face orientation, and breathing can be obtained based on lightness image 38. In the specification of detection region 62, the target portion of person 9 can be narrowed using the lightness in addition to the distance, enhancing the precision in generation of detection region 62.

Moreover, arithmetic operator 5 may generate lightness image 38 by synthesizing first image 51 and second image 52. Thereby, lightness image 38 can be generated using first image 51 and second image 52 originally obtained for estimation of the pulse, and thus, lightness image 38 can be generated without newly capturing any image.

Moreover, arithmetic operator 5 may read out first image 51 and second image 52 from imaging device 3, and may generate lightness image 38 by synthesizing first image 51 and second image 52 read out, to reproduce the arrangement positions of first elements 31 and second elements 32 in imaging device 3 where first elements 31 correspond to first image 51 and second elements 32 correspond to second image 52. Thereby, lightness image 38 is generated as one image according to the arrangement positions of the unit elements in imaging device 3 from the elements divided into two as two images for estimation of the pulse. Thus, detection region 62 can be more accurately specified using lightness image 38 having high resolution.

Moreover, arithmetic operator 5 may adjust at least one of the lightness of first image 51 or the lightness of second image 52, and synthesize first image 51 and second image 52. Thereby, the difference in the quantity of received light between first image 51 and second image 52, which is caused by the difference in reflectance between the objects within the imaging space or the difference in sensitivity between first element 31 and second element 32, can be corrected.

Moreover, first image 51 and second image 52 used in synthesis may be read out by arithmetic operator 5 after controller 4 adjusts at least one of the light quantity of first light source 21 or the light quantity of second light source 22. Thereby, the difference in quantity of received light between first element 31 and second element 32 can be corrected while the electricity needed for emission of emission light 21a and emission light 22a from the light sources is reduced.

Moreover, controller 4 may further control imaging device 3 such that imaging device 3 captures fourth images 53a and 53b when no light is emitted from first light source 21 and second light source 22. Arithmetic operator 5 may further generate third image 37 by reading out fourth images 53a and 53b from imaging device 3, fourth images 53a and 53b being captured when no light is emitted from first light source 21 and second light source 22, subtracting fourth images 53a and 53b from first image 51 and second image 52, and performing an arithmetic operation on first subtraction image 51a and second subtraction image 52a which are obtained. Thereby, influences from radiation of background light 10a can be removed, generating an image captured with only reflected light 21b and reflected light 22b of the light emitted from light source unit 2.

Moreover, arithmetic operator 5 may generate third image 37 by performing an arithmetic operation to calculate the difference or ratio between first image 51 and second image 52, and state estimator 6 may generate the biological information on the pulse of person 9 based on third image 37. Thereby, the image information captured at a wavelength can be compared with that captured at a different wavelength, influences from body moves and changes in external light can be reduced, and the information reflecting the blood flow rate during capturing of the image can be precisely obtained. Thus, the pulse and the biological information on breathing and blood pressure can be generated more precisely.

Moreover, the first wavelength and the second wavelength may be wavelengths of near-infrared light. Thereby, the light in a wavelength band having a small light quantity, such as sunlight, can be selected as background light 10a, more significantly reducing the influences from background light source 10. In addition, the near-infrared light having the wavelength highly reflective to hemoglobin can be selected and used. Furthermore, the near-infrared light is invisible light. For this reason, the biological state of the subject can be detected without illuminating the objects and the person within the imaging space, namely, without disturbing the work of the subject.

Moreover, state estimator 6 may further estimate the state of person 9 using the biological information and distance image 39. Thereby, the body move or the posture can be evaluated utilizing the distance from each body portion of person 9.

Furthermore, biological state detecting apparatus 1 may include a lens which converges reflected light 21b of the light emitted from first light source 21 and reflected light 22b of the light emitted from second light source 22 onto imaging device 3, the light emitted from first light source 21 and the light emitted from second light source 22 being reflected by person 9. When first image 51 and second image 52 correspond to the upper body of person 9, the lens may have properties to increase the magnification of imaging device 3 to project reflected light 21b and reflected light 22b onto a region corresponding to the face of person 9, compared with the magnification of imaging device 3 to project reflected light 21b and reflected light 22b onto a region corresponding to a portion of person 9 excluding the face. Thereby, the precision to capture the change can be enhanced in the biological information obtained through observation of a subtle change in the facial portion. More specifically, such precision is effective in the evaluation which requires detection of movements of small parts of the face, such as eye movement or blinking.

Moreover, the biological state detection method according to the present embodiment includes control step S101 of controlling a first light source which emits light having a first wavelength and a second light source which emits light having a second wavelength different from the first wavelength, such that the first light source and the second light source alternately emit light; arithmetic step S103 of generating a third image by reading out a first image and a second image from an imaging device including a plurality of elements which receive reflected light of the light emitted from the first light source and reflected light of the light emitted from the second light source, the light emitted from the first light source and the light emitted from the second light source being reflected by a person, and performing an arithmetic operation on the first image and the second image, the first image being obtained through reception of the reflected light of the light emitted from the first light source, the second image being obtained through reception of the reflected light of the light emitted from the second light source; and state estimation step S104 of generating the biological information of the person based on the third image generated in arithmetic step S103. In arithmetic step S103, a distance image is further generated based on at least one of the first image or the second image.

In such a configuration, the biological state detection method according to the present embodiment can estimate the pulse as the biological information, and can also obtain the information on the posture, the behavior, and the action based on distance image 39. More specifically, the posture, the behavior, and the action can be estimated through analysis of the change over time in the position of person 9 (detection target for the biological information) within the imaging space, the change over time being represented by distance image moving picture 72 of distance images 39 accumulated in storage 7. Accordingly, a biological state detection method can be provided which can generate a larger amount of biological information than that in the related art while using images.

Although biological state detecting apparatus 1 and the biological state detection method according to the present disclosure have been described above based on the embodiment, the embodiment should not be construed as limitation to the present disclosure. The present disclosure also covers a variety of modifications of the present embodiment conceived by persons skilled in the art without departing from the gist of the present disclosure, and other embodiments including any combinations of part of the components in the embodiment and its modifications.

For example, although distance image 39 is generated by synthesizing first distance image 35 and second distance image 36 in the present embodiment, only one of first distance image 35 and second distance image 36 may be used. In such a case, noises during capturing of first distance image 35 may be compared with those during capturing of second distance image 36, and the image having less noises may be used. Alternatively, the image for use may be preliminarily determined, and may be always used.

Although distance image 39 and lightness image 38 have been generated by synthesizing first image 51 and second image 52 such that the arrangement positions of first elements 31 and second elements 32 in imaging device 3 are reproduced in the present embodiment, for example, first image 51 and second image 52 may be synthesized by averaging the overlapping positions of first image 51 and second image 52, to generate distance image 39 and lightness image 38.

Although distance image 39 has been generated by the TOF method in the present embodiment, for example, distance image 39 may be generated by a stereo vision method or a structured light method.

Although detection region 62 has been specified using distance image 39 or using distance image 39 and lightness image 38 in the present embodiment, for example, detection region 62 may be specified using only lightness image 38.

Although lightness image 38 has been generated by synthesizing first lightness image 33 and second lightness image 34 in the present embodiment, for example, only one of first lightness image 33 and second lightness image 34 may be used. In such a case, noises during capturing of first lightness image 33 may be compared with those during capturing of second lightness image 34, and the image having less noises may be used. Alternatively, the image for use may be preliminarily determined, and may be always used.

Although the present embodiment has a configuration where first elements 31 are exposed to the light emitted from first light source 21 and second elements 32 are exposed to the light emitted from second light source 22, for example, the elements each including a filter through which only the light having the corresponding wavelength passes may be exposed to light at once. In this case, first light source 21 and second light source 22 emit light at the same time. Reflected light 21b of the light emitted from first light source 21 passes through the filter included in first element 31 but not through the filter included in second element 32. Thus, only the quantity of the light having the first wavelength is recorded on first element 31. Reflected light 22b of the light emitted from second light source 22 passes through the filter included in second element 32 but not through the filter included in first element 31. Thus, only the quantity of the light having the second wavelength is recorded on second element 32.

The agent of the apparatus, system, or method according to the present disclosure includes a computer. The computer executes a program to implement the function of the agent of the apparatus, system, or method according to the present disclosure. The computer includes a processor which operates according to the program, as the main hardware configuration. Any processor can be used as long as it can implement the function through execution of the program. The processor is configured of one or more electronic circuits including a semiconductor integrated circuit (IC) or large scale integration (LSI). Although it is referred to as IC or LSI here, the name changes according to the degree of integration, and may be referred to as system LSI, very large scale integration (VLSI), or ultra large scale integration (ULSI). A field programmable gate array (FPGA) programed after manufacturing of LSI or a reconfigurable logic device enabling reconfiguration of connection relations within the LSI or set up of circuit compartments within the LSI can also be used for the same purpose. Two or more electronic circuits may be integrated into a single chip, or may be disposed in two or more chips. Two or more chips may be integrated into a single device, or may be included in two or more devices. The program is recorded on a non-transitory recording medium such as a computer-readable ROM, an optical disk, or a hard disk drive. The program may be preliminarily stored in the recording medium, or may be fed to the recording medium through a wide area communication network including the Internet.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

What is claimed is:

1. A biological state detecting apparatus which detects a biological state of a person, the biological state detecting apparatus comprising:
a first light source which emits light having a first wavelength;
a second light source which emits light having a second wavelength different from the first wavelength;
an imaging device including a plurality of elements which receive reflected light of the light emitted from the first light source and reflected light of the light emitted from the second light source, the light emitted from the first light source and the light emitted from the second light source being reflected by the person;
a controller which controls the first light source and the second light source such that the first light source and the second light source alternately emit light;
an arithmetic operator which generates a third image by reading out a first image and a second image from the imaging device, and performing an arithmetic operation on the first image and the second image, the first image being obtained through reception of the reflected light of the light emitted from the first light source, the second image being obtained through reception of the reflected light of the light emitted from the second light source; and
a state estimator which generates biological information indicating a biological state of the person based on the third image generated by the arithmetic operator, and outputs the biological information,
wherein the arithmetic operator further generates a distance image based on at least one of the first image or the second image, and
wherein the state estimator includes a detection region specifier which specifies a detection region in the third image, which is a region used to generate the biological information, and generates the biological information using the detection region specified by the detection region specifier.

2. The biological state detecting apparatus according to claim 1,
wherein the arithmetic operator generates the distance image by synthesizing the first image and the second image.

3. The biological state detecting apparatus according to claim 1,
wherein the arithmetic operator generates the distance image by a time of flight method.

4. The biological state detecting apparatus according to claim 1,
wherein the detection region specifier specifies the detection region using the distance image.

5. The biological state detecting apparatus according to claim 4,
wherein the arithmetic operator further generates a lightness image based on at least one of the first image or the second image, and
the detection region specifier specifies the detection region using the distance image and the lightness image.

6. The biological state detecting apparatus according to claim 5,
wherein the arithmetic operator generates the lightness image by synthesizing the first image and the second image.

7. The biological state detecting apparatus according to claim 6,
wherein the arithmetic operator:
reads out the first image and the second image from the imaging device; and
generates the lightness image by synthesizing the first image and the second image read out, to reproduce arrangement positions of first elements and second elements in the imaging device, the first elements being included in the plurality of elements and corresponding to the first image, the second elements being included in the plurality of elements and corresponding to the second image.

8. The biological state detecting apparatus according to claim 6,
wherein the arithmetic operator adjusts at least one of a lightness of the first image or a lightness of the second image, and synthesizes the first image and the second image.

9. The biological state detecting apparatus according to claim 6,
wherein the first image and the second image used in the synthesis are read out by the arithmetic operator after the controller adjusts at least one of a light quantity of the first light source or a light quantity of the second light source.

10. The biological state detecting apparatus according to claim 1,
wherein the controller further controls the imaging device such that the imaging device captures at least one fourth image when no light is emitted from the first light source and the second light source, and
the arithmetic operator further generates the third image by reading out the at least one fourth image from the imaging device, subtracting the at least one fourth image from the first image and the second image, and performing an arithmetic operation on a first subtraction image and a second subtraction image which are obtained.

11. The biological state detecting apparatus according to claim 1,
wherein the arithmetic operator generates the third image by performing an arithmetic operation to calculate a difference or ratio between the first image and the second image, and
the state estimator generates biological information on a pulse of the person based on the third image.

12. The biological state detecting apparatus according to claim 1,
wherein the first wavelength and the second wavelength are wavelengths of near-infrared light.

13. The biological state detecting apparatus according to claim 1,
wherein the state estimator further estimates a state of the person using the biological information and the distance image.

14. The biological state detecting apparatus according to claim 1, further comprising:

a lens which converges the reflected light of the light emitted from the first light source and the reflected light of the light emitted from the second light source onto the imaging device, the light emitted from the first light source and the light emitted from the second light source being reflected by the person, wherein when the first image and the second image correspond to an upper body of the person, the lens has properties to increase a magnification of the imaging device to project the reflected light onto a region corresponding to a face of the person, compared to a magnification of the imaging device to project the reflected light onto a region corresponding to a portion of the person excluding the face.

15. A biological state detecting apparatus which detects a biological state of a person, the biological state detecting apparatus comprising:

a first light source which emits light having a first wavelength;

a second light source which emits light having a second wavelength different from the first wavelength;

an imaging device including a plurality of elements which receive reflected light of the light emitted from the first light source and reflected light of the light emitted from the second light source, the light emitted from the first light source and the light emitted from the second light source being reflected by the person;

a controller which controls the first light source and the second light source such that the first light source and the second light source alternately emit light;

an arithmetic operator which generates a third image by reading out a first image and a second image from the imaging device, and performing an arithmetic operation on the first image and the second image, the first image being obtained through reception of the reflected light of the light emitted from the first light source, the second image being obtained through reception of the reflected light of the light emitted from the second light source; and a state estimator which generates biological information indicating a biological state of the person based on the third image generated by the arithmetic operator, and outputs the biological information, wherein the arithmetic operator further generates a distance image based on at least one of the first image or the second image, wherein the arithmetic operator generates the distance image by synthesizing the first image and the second image, and wherein the arithmetic operator:

reads out the first image and the second image from the imaging device; and generates the distance image by synthesizing the first image and the second image read out, to reproduce arrangement positions of first elements and second elements in the imaging device, the first elements being included in the plurality of elements and corresponding to the first image, the second elements being included in the plurality of elements and corresponding to the second image.

16. A biological state detection method of detecting a biological state of a person, the biological state detection method comprising:

controlling a first light source which emits light having a first wavelength and a second light source which emits light having a second wavelength different from the first wavelength, such that the first light source and the second light source alternately emit light;

generating a third image by reading out a first image and a second image from an imaging device including a plurality of elements which receive reflected light of the light emitted from the first light source and reflected light of the light emitted from the second light source, the light emitted from the first light source and the light emitted from the second light source being reflected by the person, and performing an arithmetic operation on the first image and the second image, the first image being obtained through reception of the reflected light of the light emitted from the first light source, the second image being obtained through reception of the reflected light of the light emitted from the second light source; and generating biological information indicating a biological state of the person based on the third image, wherein in the generating of the third image, a distance image is further generated based on at least one of the first image or the second image, and wherein a detection region in the third image, which is a region used to generate the biological information, is specified and the biological information is generated using the detection region specified.

* * * * *